US008795169B2

(12) United States Patent
Cosentino et al.

(10) Patent No.: US 8,795,169 B2
(45) Date of Patent: Aug. 5, 2014

(54) APPARATUS AND METHOD FOR MONITORING AND COMMUNICATING WELLNESS PARAMETERS OF AMBULATORY PATIENTS

(75) Inventors: Louis C. Cosentino, Excelsior, MN (US); Michael John Duea, Savage, MN (US); Duane Robert Duea, Apple Valley, MN (US); Steven George Dorfe, Maple Grove, MN (US); Richard C. Nubson, Eden Prairie, MN (US); Judith A. Cosentino, Excelsior, MN (US)

(73) Assignee: Cardiocom, LLC, Minneapolis, MN (US)

( * ) Notice: Subject to any disclaimer, the term of this patent is extended or adjusted under 35 U.S.C. 154(b) by 0 days.

(21) Appl. No.: 10/719,408

(22) Filed: Nov. 21, 2003

(65) Prior Publication Data

US 2004/0102685 A1 May 27, 2004

Related U.S. Application Data

(60) Continuation of application No. 09/918,247, filed on Jul. 30, 2001, now Pat. No. 6,723,045, which is a division of application No. 09/293,619, filed on Apr. 16, 1999, now Pat. No. 6,290,646.

(51) Int. Cl.
*A61B 5/00* (2006.01)
*G06F 19/00* (2011.01)

(52) U.S. Cl.
CPC .................................. *G06F 19/3431* (2013.01)
USPC ............................................... 600/301; 705/2

(58) Field of Classification Search
USPC ......... 600/300–301, 407, 481–486, 500–508, 600/544, 547; 128/903, 904, 920–925; 705/2–4; 434/236–238, 262; 340/573
See application file for complete search history.

(56) References Cited

U.S. PATENT DOCUMENTS 3,743,040 A 7/1973 Hutchinson et al.
3,907,503 A 9/1975 Betts et al.
(Continued)

FOREIGN PATENT DOCUMENTS

DE 43 35 869 A1 10/1994
EP 0 251 520 A2 1/1988
(Continued)

OTHER PUBLICATIONS

Patel, U. et al., "A Computer-Based, Automated, Telephonic System to Monitor Patient Progress in the Home Setting", *Journal of Medical Systems*, vol. 16, Nos. 2/3, pp. 101-112 (1992).
(Continued)

*Primary Examiner* — Gary Jackson
*Assistant Examiner* — Bobby Soriano
(74) *Attorney, Agent, or Firm* — Girma Wolde-Michael; Evans M. Mburu

(57) ABSTRACT

The monitoring device incorporates transducing devices for converting the desired measured parameters into electrical signals capable of being processed by a local computer or microprocessor system. The device interacts with the ambulatory patient and then, via a modem or other electronic communication device, transmits the measured parameters to a computer located at a remote site. At the remote location, the various indicia of the ambulatory patient's condition are monitored and analyzed by the medical professional caregiver. To provide the ambulatory patient with an added level of convenience and ease of use, such monitoring device is contained in a single integrated package.

28 Claims, 10 Drawing Sheets

(56) References Cited

U.S. PATENT DOCUMENTS

| | | | |
|---|---|---|---|
| 3,925,762 A | 12/1975 | Heitlinger et al. | |
| 4,144,306 A | 3/1979 | Figueras | |
| 4,328,396 A | 5/1982 | Theis | |
| 4,476,149 A | 10/1984 | Poppe et al. | |
| 4,510,383 A | 4/1985 | Ruppender | |
| 4,531,527 A | 7/1985 | Reinhold, Jr. et al. | |
| 4,535,782 A | 8/1985 | Zoltan | |
| 4,556,866 A | 12/1985 | Gorecki | |
| 4,576,244 A | 3/1986 | Zeigner et al. | |
| 4,592,893 A | 6/1986 | Poppe et al. | |
| RE32,361 E | 2/1987 | Duggan | |
| 4,712,562 A | 12/1987 | Ohayon et al. | |
| 4,724,521 A | 2/1988 | Carron et al. | |
| 4,803,625 A | 2/1989 | Fu et al. | |
| 4,835,372 A | 5/1989 | Gombrich et al. | |
| 4,838,275 A | 6/1989 | Lee | |
| 4,844,187 A * | 7/1989 | Jabero | 177/5 |
| 4,877,580 A | 10/1989 | Aronowitz et al. | |
| 4,899,758 A | 2/1990 | Finkelstein et al. | |
| 4,916,441 A | 4/1990 | Gombrich | |
| 4,935,346 A | 6/1990 | Phillips et al. | |
| 4,947,858 A | 8/1990 | Smith | |
| 4,998,534 A * | 3/1991 | Claxton et al. | 600/483 |
| 5,012,411 A | 4/1991 | Policastro et al. | |
| 5,019,974 A | 5/1991 | Beckers | |
| 5,054,493 A | 10/1991 | Cohn et al. | |
| 5,092,330 A | 3/1992 | Duggan | |
| 5,113,869 A | 5/1992 | Nappholz et al. | |
| 5,212,546 A | 5/1993 | Arazi et al. | |
| 5,241,966 A | 9/1993 | Finkelstein et al. | |
| 5,265,010 A | 11/1993 | Evans-Paganelli et al. | |
| 5,265,605 A | 11/1993 | Afflerbach | |
| 5,281,395 A | 1/1994 | Markart et al. | |
| 5,307,263 A | 4/1994 | Brown | |
| 5,331,549 A | 7/1994 | Crawford, Jr. | |
| 5,339,821 A | 8/1994 | Fujimoto | |
| 5,341,291 A | 8/1994 | Roizen et al. | |
| 5,367,667 A | 11/1994 | Wahlquist et al. | |
| 5,379,057 A | 1/1995 | Clough et al. | |
| 5,390,238 A | 2/1995 | Kirk et al. | |
| 5,402,794 A | 4/1995 | Wahlstrand et al. | |
| 5,406,955 A | 4/1995 | Bledsoe et al. | |
| 5,434,611 A | 7/1995 | Tamura | |
| 5,437,285 A | 8/1995 | Verrier et al. | |
| 5,441,047 A | 8/1995 | David et al. | |
| 5,465,082 A | 11/1995 | Chaco | |
| 5,467,773 A | 11/1995 | Bergelson et al. | |
| 5,471,382 A * | 11/1995 | Tallman et al. | 600/300 |
| 5,486,999 A * | 1/1996 | Mebane | 705/2 |
| 5,515,170 A | 5/1996 | Matzinger et al. | |
| 5,522,396 A | 6/1996 | Langer et al. | |
| 5,549,117 A | 8/1996 | Tacklind et al. | |
| 5,549,654 A | 8/1996 | Powell | |
| 5,553,609 A | 9/1996 | Chen et al. | |
| 5,553,623 A | 9/1996 | Ochs | |
| 5,558,638 A | 9/1996 | Evers et al. | |
| 5,560,370 A | 10/1996 | Verrier et al. | |
| 5,563,031 A | 10/1996 | Yu | |
| 5,573,551 A | 11/1996 | Lin et al. | |
| 5,583,758 A | 12/1996 | McIlroy et al. | |
| 5,584,868 A | 12/1996 | Salo et al. | |
| 5,586,557 A | 12/1996 | Nelson et al. | |
| 5,590,648 A | 1/1997 | Mitchell et al. | |
| 5,594,638 A | 1/1997 | Iliff | |
| 5,619,991 A | 4/1997 | Sloane | |
| 5,622,178 A | 4/1997 | Gilham | |
| 5,623,656 A | 4/1997 | Lyons | |
| 5,633,910 A | 5/1997 | Cohen | |
| 5,635,060 A | 6/1997 | Hagen et al. | |
| 5,642,731 A * | 7/1997 | Kehr | 600/300 |
| 5,660,176 A | 8/1997 | Iliff | |
| 5,673,691 A | 10/1997 | Abrams et al. | |
| 5,684,826 A | 11/1997 | Ratner | |
| 5,687,717 A | 11/1997 | Halpern et al. | |
| 5,704,029 A | 12/1997 | Wright, Jr. | |
| 5,704,364 A | 1/1998 | Saltzstein et al. | |
| 5,704,366 A | 1/1998 | Tacklind et al. | |
| 5,711,297 A | 1/1998 | Iliff | |
| 5,724,032 A | 3/1998 | Klein et al. | |
| 5,724,968 A | 3/1998 | Iliff | |
| 5,725,559 A | 3/1998 | Alt et al. | |
| 5,743,267 A | 4/1998 | Nikolic et al. | |
| 5,745,555 A | 4/1998 | Mark | |
| 5,758,652 A | 6/1998 | Nikolic | |
| 5,771,511 A | 6/1998 | Kummer et al. | |
| 5,778,882 A | 7/1998 | Raymond et al. | |
| 5,781,442 A | 7/1998 | Engleson et al. | |
| 5,822,715 A | 10/1998 | Worthington et al. | |
| 5,827,180 A | 10/1998 | Goodman | |
| 5,828,943 A | 10/1998 | Brown | |
| 5,832,448 A | 11/1998 | Brown | |
| 5,839,438 A | 11/1998 | Graettinger et al. | |
| 5,842,997 A | 12/1998 | Verrier et al. | |
| 5,843,139 A | 12/1998 | Goedeke et al. | |
| 5,846,223 A | 12/1998 | Swartz et al. | |
| 5,868,669 A | 2/1999 | Iliff | |
| 5,874,988 A | 2/1999 | Gu | |
| 5,876,353 A | 3/1999 | Riff | |
| 5,879,163 A | 3/1999 | Brown et al. | |
| 5,890,128 A | 3/1999 | Diaz et al. | |
| 5,897,493 A | 4/1999 | Brown | |
| 5,899,855 A | 5/1999 | Brown | |
| 5,910,107 A | 6/1999 | Iliff | |
| 5,911,687 A | 6/1999 | Sato et al. | |
| 5,913,310 A | 6/1999 | Brown | |
| 5,918,603 A | 7/1999 | Brown | |
| 5,931,791 A | 8/1999 | Saltzstein et al. | |
| 5,933,136 A | 8/1999 | Brown | |
| 5,935,060 A | 8/1999 | Iliff | |
| 5,951,300 A | 9/1999 | Brown | |
| 5,956,683 A | 9/1999 | Jacobs et al. | |
| 5,957,861 A | 9/1999 | Combs et al. | |
| 5,960,403 A | 9/1999 | Brown | |
| 5,964,700 A * | 10/1999 | Tallman et al. | 600/300 |
| 5,967,979 A | 10/1999 | Taylor et al. | |
| 5,985,559 A | 11/1999 | Brown | |
| 5,987,519 A | 11/1999 | Peifer et al. | |
| 5,989,917 A | 11/1999 | McAleer et al. | |
| 5,997,476 A | 12/1999 | Brown | |
| 6,007,493 A | 12/1999 | Ericksen et al. | |
| 6,014,626 A | 1/2000 | Cohen | |
| 6,022,315 A | 2/2000 | Iliff | |
| 6,024,699 A * | 2/2000 | Surwit et al. | 600/300 |
| 6,032,119 A | 2/2000 | Brown et al. | |
| 6,038,465 A * | 3/2000 | Melton, Jr. | 600/407 |
| 6,045,513 A | 4/2000 | Stone et al. | |
| 6,059,724 A * | 5/2000 | Campell et al. | 600/300 |
| 6,063,028 A * | 5/2000 | Luciano | 600/300 |
| 6,071,236 A | 6/2000 | Iliff | |
| 6,080,106 A | 6/2000 | Lloyd et al. | |
| 6,085,162 A | 7/2000 | Cherny | |
| 6,088,429 A | 7/2000 | Garcia | |
| 6,101,478 A | 8/2000 | Brown | |
| 6,112,224 A | 8/2000 | Peifer et al. | |
| 6,113,540 A | 9/2000 | Iliff | |
| 6,117,073 A | 9/2000 | Jones et al. | |
| 6,120,440 A * | 9/2000 | Goknar | 600/300 |
| 6,126,596 A | 10/2000 | Freedman | |
| 6,144,837 A | 11/2000 | Quy | |
| 6,148,233 A | 11/2000 | Owen et al. | |
| 6,151,581 A * | 11/2000 | Kraftson et al. | 705/3 |
| 6,167,362 A | 12/2000 | Brown et al. | |
| 6,168,563 B1 | 1/2001 | Brown | |
| 6,168,957 B1 | 1/2001 | Matzinger et al. | |
| 6,171,237 B1 * | 1/2001 | Avitall et al. | 600/300 |
| 6,177,940 B1 * | 1/2001 | Bond et al. | 434/262 |
| 6,217,744 B1 | 4/2001 | Crosby | |
| 6,234,964 B1 * | 5/2001 | Iliff | 600/300 |
| 6,240,393 B1 | 5/2001 | Brown | |
| 6,246,992 B1 | 6/2001 | Brown | |
| 6,248,065 B1 | 6/2001 | Brown | |
| 6,269,339 B1 * | 7/2001 | Silver | 705/2 |
| 6,270,456 B1 | 8/2001 | Iliff | |
| 6,277,071 B1 | 8/2001 | Hennessy et al. | |

(56) References Cited

U.S. PATENT DOCUMENTS

| | | | |
|---|---|---|---|
| 6,283,923 B1 | 9/2001 | Finkelstein et al. | |
| 6,290,646 B1 | 9/2001 | Cosentino et al. | |
| 6,295,506 B1 | 9/2001 | Heinonen et al. | |
| 6,328,699 B1 | 12/2001 | Eigler et al. | |
| 6,336,900 B1* | 1/2002 | Alleckson et al. | 600/485 |
| 6,354,996 B1 | 3/2002 | Drinan et al. | |
| 6,368,273 B1 | 4/2002 | Brown | |
| 6,398,727 B1* | 6/2002 | Bui et al. | 600/300 |
| 6,402,691 B1 | 6/2002 | Peddicord et al. | |
| 6,413,213 B1 | 7/2002 | Essenpreis et al. | |
| 6,416,471 B1* | 7/2002 | Kumar et al. | 600/300 |
| 6,454,705 B1 | 9/2002 | Cosentino et al. | |
| 6,473,638 B2 | 10/2002 | Ferek-Petric | |
| 6,477,424 B1 | 11/2002 | Thompson et al. | |
| 6,493,568 B1* | 12/2002 | Bell et al. | 600/323 |
| 6,541,266 B2 | 4/2003 | Modzelewski et al. | |
| 6,558,321 B1 | 5/2003 | Burd et al. | |
| 6,612,985 B2 | 9/2003 | Eiffert et al. | |
| 6,641,533 B2 | 11/2003 | Causey, III et al. | |
| 6,723,045 B2 | 4/2004 | Cosentino et al. | |
| 6,755,783 B2 | 6/2004 | Cosentino et al. | |
| 6,757,898 B1 | 6/2004 | Ilsen et al. | |
| 6,770,487 B2 | 8/2004 | Crosby | |
| 6,780,645 B2 | 8/2004 | Hayter et al. | |
| 6,814,844 B2 | 11/2004 | Bhullar et al. | |
| 6,849,045 B2* | 2/2005 | Iliff | 600/300 |
| 6,849,237 B2 | 2/2005 | Housefield et al. | |
| 6,891,936 B2 | 5/2005 | Kai et al. | |
| 6,968,375 B1 | 11/2005 | Brown | |
| 7,004,928 B2 | 2/2006 | Aceti et al. | |
| 7,056,289 B2 | 6/2006 | Kasper et al. | |
| 7,127,290 B2 | 10/2006 | Girouard et al. | |
| 7,215,991 B2 | 5/2007 | Besson et al. | |
| 7,223,236 B2 | 5/2007 | Brown | |
| 7,252,636 B2 | 8/2007 | Brown | |
| 7,299,081 B2 | 11/2007 | Mace et al. | |
| 7,319,962 B2 | 1/2008 | Goedeke et al. | |
| 7,401,413 B1 | 7/2008 | Nelson | |
| 7,433,853 B2 | 10/2008 | Brockway et al. | |
| 7,478,434 B1 | 1/2009 | Hinton et al. | |
| 7,577,475 B2 | 8/2009 | Cosentino et al. | |
| 7,624,028 B1 | 11/2009 | Brown | |
| 7,647,234 B1 | 1/2010 | Ruderman et al. | |
| 7,733,224 B2 | 6/2010 | Tran | |
| 7,736,318 B2 | 6/2010 | Cosentino et al. | |
| 7,827,040 B2 | 11/2010 | Brown | |
| 7,941,327 B2 | 5/2011 | Brown | |
| 7,945,451 B2 | 5/2011 | Cosentino et al. | |
| 7,972,266 B2 | 7/2011 | Gobeyn et al. | |
| 8,015,025 B2 | 9/2011 | Brown | |
| 8,034,294 B1 | 10/2011 | Goldberg | |
| 8,140,663 B2 | 3/2012 | Brown | |
| 8,419,650 B2 | 4/2013 | Cosentino et al. | |
| 8,438,038 B2 | 5/2013 | Cosentino et al. | |
| 8,525,643 B2 | 9/2013 | Green et al. | |
| 8,532,775 B2 | 9/2013 | Berg et al. | |
| 2001/0020229 A1* | 9/2001 | Lash | 705/3 |
| 2001/0029322 A1 | 10/2001 | Iliff | |
| 2001/0032099 A1 | 10/2001 | Joao | |
| 2001/0048529 A1 | 12/2001 | Fotland | |
| 2001/0053875 A1 | 12/2001 | Iliff | |
| 2001/0056229 A1 | 12/2001 | Cosentino et al. | |
| 2002/0010597 A1 | 1/2002 | Mayer et al. | |
| 2002/0018478 A1 | 2/2002 | Takeyama et al. | |
| 2002/0019747 A1 | 2/2002 | Ware et al. | |
| 2002/0022973 A1 | 2/2002 | Sun et al. | |
| 2002/0082480 A1 | 6/2002 | Riff et al. | |
| 2002/0082665 A1 | 6/2002 | Haller et al. | |
| 2002/0111539 A1 | 8/2002 | Cosentino et al. | |
| 2002/0133502 A1 | 9/2002 | Rosenthal et al. | |
| 2002/0147423 A1 | 10/2002 | Burbank et al. | |
| 2002/0156650 A1 | 10/2002 | Klein et al. | |
| 2002/0158775 A1 | 10/2002 | Wallace | |
| 2002/0173991 A1 | 11/2002 | Avitall | |
| 2003/0001742 A1 | 1/2003 | Eshelman et al. | |
| 2003/0004758 A1 | 1/2003 | Luttrell | |
| 2003/0028399 A1 | 2/2003 | Davis et al. | |
| 2003/0050054 A1 | 3/2003 | Siu | |
| 2003/0069753 A1 | 4/2003 | Brown | |
| 2003/0083556 A1 | 5/2003 | Cosentino et al. | |
| 2003/0229517 A1 | 12/2003 | Meserol et al. | |
| 2004/0015191 A1 | 1/2004 | Otman et al. | |
| 2004/0034286 A1 | 2/2004 | Kasper et al. | |
| 2004/0078220 A1 | 4/2004 | Jackson | |
| 2004/0117204 A1 | 6/2004 | Mazar et al. | |
| 2004/0122297 A1 | 6/2004 | Stahmann et al. | |
| 2004/0139048 A1 | 7/2004 | Kerr, II et al. | |
| 2004/0147969 A1 | 7/2004 | Mann et al. | |
| 2004/0147982 A1 | 7/2004 | Bardy | |
| 2004/0172080 A1 | 9/2004 | Stadler et al. | |
| 2004/0199409 A1 | 10/2004 | Brown | |
| 2004/0220832 A1 | 11/2004 | Moll et al. | |
| 2004/0225533 A1 | 11/2004 | Cosentino et al. | |
| 2004/0236187 A1 | 11/2004 | Bock et al. | |
| 2004/0260666 A1 | 12/2004 | Pestotnik et al. | |
| 2005/0015115 A1 | 1/2005 | Sullivan et al. | |
| 2005/0033127 A1 | 2/2005 | Ciurczak et al. | |
| 2005/0038332 A1 | 2/2005 | Saidara et al. | |
| 2005/0065813 A1 | 3/2005 | Mishelevich et al. | |
| 2005/0075116 A1 | 4/2005 | Laird et al. | |
| 2005/0172021 A1 | 8/2005 | Brown | |
| 2005/0192487 A1 | 9/2005 | Cosentino et al. | |
| 2005/0231375 A1 | 10/2005 | Kingston | |
| 2005/0279631 A1 | 12/2005 | Celentano | |
| 2006/0015017 A1 | 1/2006 | Cosentino et al. | |
| 2006/0030890 A1 | 2/2006 | Cosentino et al. | |
| 2006/0064030 A1 | 3/2006 | Cosentino et al. | |
| 2006/0106290 A1 | 5/2006 | Bulat | |
| 2006/0161457 A1 | 7/2006 | Rapaport et al. | |
| 2006/0247985 A1 | 11/2006 | Liamos et al. | |
| 2006/0248398 A1 | 11/2006 | Neel et al. | |
| 2006/0271445 A1 | 11/2006 | Lee et al. | |
| 2007/0011465 A1 | 1/2007 | Webber et al. | |
| 2007/0021979 A1 | 1/2007 | Cosentino et al. | |
| 2007/0073590 A1 | 3/2007 | Cosentino et al. | |
| 2007/0118422 A1 | 5/2007 | Berger et al. | |
| 2007/0155588 A1 | 7/2007 | Stark et al. | |
| 2007/0231209 A1 | 10/2007 | Cosentino et al. | |
| 2007/0231846 A1 | 10/2007 | Cosentino et al. | |
| 2008/0117060 A1 | 5/2008 | Cuddihy et al. | |
| 2008/0262871 A1 | 10/2008 | Lee et al. | |
| 2008/0294024 A1 | 11/2008 | Cosentino et al. | |
| 2009/0037216 A1 | 2/2009 | Bluemler et al. | |
| 2009/0138207 A1 | 5/2009 | Cosentino et al. | |
| 2009/0138717 A1 | 5/2009 | Calamera et al. | |
| 2009/0192362 A1 | 7/2009 | Sweeney | |
| 2009/0204028 A1 | 8/2009 | Richards | |
| 2009/0216558 A1 | 8/2009 | Reisman et al. | |
| 2009/0234916 A1 | 9/2009 | Cosentino et al. | |
| 2010/0005416 A1 | 1/2010 | Hedmann et al. | |
| 2010/0113891 A1 | 5/2010 | Barrett et al. | |
| 2010/0121201 A1 | 5/2010 | Papaioannou | |
| 2010/0137693 A1 | 6/2010 | Porras et al. | |
| 2010/0249536 A1 | 9/2010 | Cosentino et al. | |
| 2010/0295684 A1 | 11/2010 | Hsieh et al. | |
| 2011/0098539 A1 | 4/2011 | Estocado | |
| 2011/0105979 A1 | 5/2011 | Schlaeper et al. | |
| 2011/0125532 A1 | 5/2011 | Cosentino et al. | |
| 2011/0307284 A1 | 12/2011 | Thompson et al. | |
| 2012/0041771 A1 | 2/2012 | Cosentino et al. | |
| 2012/0041775 A1 | 2/2012 | Cosentino et al. | |
| 2012/0323796 A1 | 12/2012 | Udani | |
| 2013/0043997 A1 | 2/2013 | Cosentino et al. | |
| 2013/0082837 A1 | 4/2013 | Cosentino et al. | |
| 2013/0131574 A1 | 5/2013 | Cosentino et al. | |
| 2013/0267795 A1 | 10/2013 | Cosentino et al. | |
| 2013/0297344 A1 | 11/2013 | Cosentino et al. | |
| 2013/0332730 A1 | 12/2013 | Cosentino et al. | |
| 2014/0006054 A1 | 1/2014 | Cosentino et al. | |

FOREIGN PATENT DOCUMENTS

| | | |
|---|---|---|
| EP | 0 256 806 A2 | 2/1988 |
| EP | 0 290 610 A1 | 11/1988 |

(56) References Cited

FOREIGN PATENT DOCUMENTS

| | | |
|---|---|---|
| EP | 0 505 627 A2 | 9/1992 |
| EP | 0 890 919 A1 | 1/1999 |
| EP | 0 896 828 | 2/1999 |
| EP | 1 147 739 A2 | 10/2001 |
| EP | 0 880 407 B1 | 4/2002 |
| EP | 1 416 417 A2 | 5/2004 |
| EP | 1 547 516 A1 | 6/2005 |
| JP | 01006865 A | 1/1989 |
| JP | 09173304 | 7/1997 |
| WO | WO 94/24929 | 11/1994 |
| WO | WO 96/13707 | 5/1996 |
| WO | WO 97/29847 | 8/1997 |
| WO | WO 98/18211 | 4/1998 |
| WO | WO 98/38909 | 9/1998 |
| WO | WO 98/40835 | 9/1998 |
| WO | WO 98/50873 | 11/1998 |
| WO | WO 98/58338 | 12/1998 |
| WO | WO 99/04043 | 1/1999 |
| WO | WO 99/22236 | 5/1999 |
| WO | WO 99/25110 | 5/1999 |
| WO | WO 00/33072 | 6/2000 |
| WO | WO 00/41613 | 7/2000 |
| WO | WO 00/62662 | 10/2000 |
| WO | WO 01/00086 A1 | 1/2001 |
| WO | WO 01/21065 A1 | 3/2001 |
| WO | WO 01/22343 | 3/2001 |
| WO | WO 01/39089 A1 | 5/2001 |
| WO | WO 01/69513 A2 | 9/2001 |
| WO | WO 01/74229 A2 | 10/2001 |
| WO | WO 01/89363 A2 | 11/2001 |
| WO | WO 03/005891 A1 | 1/2003 |
| WO | WO 03/075756 A1 | 9/2003 |
| WO | WO 2004/106885 A2 | 12/2004 |
| WO | WO 2004/113911 A1 | 12/2004 |
| WO | WO 2005/040793 A1 | 5/2005 |
| WO | WO 2007/044877 A2 | 4/2007 |
| WO | WO 2012/021240 A2 | 2/2012 |

OTHER PUBLICATIONS

"Technology to Help Meet Standards and Reduce Costs", Alere Medical Incorporated, 6 pages (1998).
"Telemedicine, Your Partner in Telemedicine", Aerotel Medical Systems, Ltd., Internet at http://www.aerotel.com/telemed/under.html, last updated Sep. 5, 1998.
"Telemedicine NEW: BP-TEL™ Transtelephonic Blood Pressure: Your Partner in Telemedicine", http://www.aerotel.corn/telemed/, 2 pgs. (Feb. 6, 2001) last updated.
Yazolino, L., "Effective, Daily At-home Monitoring of Chronically Ill Patients," *Medical Electronics*, 4 pages (Sep. 1998).
International Search Report for International Application No. PCT/US 03/07099, 8 pp., Jul. 22, 2003.
"Thin-Link: Like Having a Personal Coach and Dietitian in Your Home Every Day," http://web.archive.org/web/20041009141519/www.thin-link.com/program_weightloss.html, 2 pages (Date Printed Aug. 31, 2005).
Teixeira, P. et al., "Weight Loss Readiness in Middle-Aged Women: Psychosocial Predictors of Success for Behavioral Weight Reduction," *Journal of Behavioral Medicine*, vol. 25, No. 6, pp. 499-523 (Dec. 2002).
Lüthje, L. et al., "Detection of heart failure decomposition using intrathoracic impedance monitoring by a triple-chamber implantable defibrillator," *Heart Rhythm*, vol. 2, No. 9, pp. 997-999 (Sep. 2005).
Bittorf et al., "Teaching Resources for Dermatology on the WWW—Quiz System and Dynamic Lecture Scripts using a HTTP-Database Demon," *Proc AMIA Annu Fall Symp.*, pp. 46-50 (1996).
Request for Ex Parte Reexamination Filed Nov. 9, 2007, 25 pages.
Request for Inter Parties Reexamination Filed Aug. 1, 2008, 126 pages.
Action Closing Prosecution for U.S. Appl. No. 90/010,053 and U.S. Appl. No. 95/000,386, dated Jan. 17, 2012, 57 pages.
Excerpts from File History of U.S. Patent No. 6,968,375, filed Sep. 8, 2000, Stephen J. Brown (339 pages).
Excerpts from File History of U.S. Patent No. 7,252,636, filed Jun. 13, 2005, Stephen J. Brown (336 pages).
Excerpts from File History of U.S. Patent No. 8,015,025, filed Nov. 15, 2006, Stephen J. Brown (271 pages).
Excerpts from File History of U.S. Patent No. 8,140,663, filed Jun. 13, 2005, 505 pages.
File History of Reexam U.S. Appl. No. 90/009,281, Filed Sep. 23, 2008, Stephn J. Brown, 646 pages.
File History of U.S. Patent No. 6,368,273, filed Apr. 28, 1999, Stephen J. Brown, 407 pages.
U.S. Appl. No. 90/009,281, Notice of Intent to issue a Reexamination Certificate, dated Mar. 16, 2010, 7 pages.
EPO Communication pursuant to Rules 161(1) and 162 EPC for Application No. 09764994.1, dated Jul. 22, 2011.
First Communication from European Patent Application No. 08767827.2 dated Sep. 28, 2011.
European Search Report for Application No. 02768819.1, 3 pages, mailed Feb. 23, 2005.
European Search Report for Application No. 10151955.1, 5 pages, mailed Aug. 10, 2010.
European Search Report for Application No. 10166822.6, 5 pages, mailed Sep. 14, 2010.
European Search Report for Application No. 10181162.8, 7 pages, mailed Jan. 12, 2011.
European Search Report for Application No. 08767827.2 (PCT/US2008/006453), 7 pages, mailed Mar. 21, 2011.
European Search Report for Application No. 10181851.6, 4 pages, mailed Jul. 22, 2011.
European Search Report for Application No. 10181855.7, 5 pages, mailed Jul. 22, 2011.
European Search Report for Application No. 11168162.3, 6 pages, mailed Jul. 28, 2011.
European Search Report for Application No. 11167368.7, 7 pages, mailed Sep. 29, 2011.
European Search Report for Application No. 11167369.5, 9 pages, mailed Oct. 6, 2011.
Groner et al., "An Introduction to the CLINFO Prototype Data Management and Analysis System", R-1541-NIH, 69 pages (Dec. 1977).
Hughes, S., "Bedside Terminals: Clinicom," *Clinical Computing*, vol. 5, No. 1 pp. 3 and 22-28 (1988).
International Preliminary Report on Patentability for PCT/US2010/030497, 8 pages, mailed Aug. 25, 2011.
International Search Report for International Application No. PCT/US00/24425, 8 pages, mailed Jan. 2, 2002.
International Search Report for International Application No. PCT/US02/28465, 6 pages, mailed Dec. 10, 2002.
International Search Report and Written Opinion for International Application No. PCT/US2004/041122, 13 pages, mailed Sep. 15, 2005.
International Search Report and Written Opinion for International Application No. PCT/US2005/005739, 13 pages, mailed Oct. 24, 2005.
International Search Report and Written Opinion for International Application No. PCT/US2006/036407, 12 pages, mailed Jan. 23, 2007.
International Search Report and Written Opinion for International Application No. PCT/US2007/008223, 14 pages, mailed Aug. 23, 2007.
International Search Report and Written Opinion for International Application No. PCT/US2007/002556, 17 pages, mailed May 28, 2008.
International Search Report and Written Opinion for International Application No. PCT/US2007/008250, 16 pages, mailed Jun. 23, 2008.
International Search Report and Written Opinion for International Application No. PCT/US08/06453, 12 pages, mailed Sep. 29, 2008.
International Search Report and Written Opinion for International Application No. PCT/US2009/067090, 14 pages, mailed Feb. 12, 2010.

(56) References Cited

OTHER PUBLICATIONS

International Search Report and Written Opinion for International Application No. PCT/US2010/030497, 16 pages, mailed Jul. 27, 2010.
International Search Report and Written Opinion for International Application No. PCT/US2011/043643, 8 pages, mailed Sep. 23, 2011.
International Search Report and Written Opinion for International Application No. PCT/US2012/037571, 12 pages, mailed Aug. 31, 2012.
International Search Report and Written Opinion for International Application No. PCT/US2012/057896, 11 pages, mailed Feb. 13, 2013.
International Search Report and Written Opinion for International Application No. PCT/US2012/038386 mailed Jul. 11, 2013.
International Search Report and Written Opinion for International Application No. PCT/US2013/044954 mailed Sep. 20, 2013.
International Search Report and Written Opinion for International Application No. PCT/US13/46375 mailed Jan. 10, 2014.
Invitation to Pay Additional Fees with Partial International Search for International Application No. PCT/US2006/027440, 8 pages, mailed Mar. 8, 2007.
Invitation to Pay Additional Fees with Partial International Search for International Application No. PCT/US2007/002556, 8 pages, mailed Apr. 3, 2008.
Invitation to Pay Additional Fees with Partial International Search for International Application No. PCT/US2007/008250, 9 pages, mailed Apr. 16, 2008.
Invitation to Pay Additional Fees with Partial International Search for International Application No. PCT/US2013/035271, 6 pages, mailed Nov. 4, 2013.
Lobach, D., "Electronically Distributed, Computer-Generated, Individualized Feedback Enhances the Use of a Computerized Practice Guideline," *Proc. Annu. Symp. Comput. Appl. Med. Care*, pp. 493-497 (1996).
Lobach, D. et al., "Computerized Decision Support Based on a Clinical Practice Guideline Improves Compliance with Care Standards," *The American Journal of Medicine*, vol. 102, pp. 89-98 (Jan. 1997).
Lobach, D. et al., "Development and Evaluation of a Computer-Assisted Management Protocol (CAMP): Improved Compliance with Care Guidelines for Diabetes Mellitus," *Proc. Annu. Symp. Comput. Appl. Med. Care*, pp. 787-791 (1994).
Nilasena, D. et al., "A Computer-Generated Reminder System Improves Physician Cmopliance with Diabetes Preventive Care Guidelines," *Proc. Annu. Symp. Comput. Appl. Med. Care*, pp. 640-645 (1995).
Schrezenmeier, J. et al., "Computer Assisted Insulin Dosage Adjustment — Perspectives for Diabetes Control," *Hormone and Metabolic Research, Supplemental Series*, vol. 24, pp. 116-123 (1990).
Vincent et al., "The Effects of a Computer-Assisted Reminder System on Patient Compliance With Recommended Health Maintenance Procedures", Proc. Annu. Symp. Comput. Appl. Med. Care, pp. 656-660 (1995).
Webster's Ninth New Collegiate Dictionary Definition of "Computer", 4 pages (1990).

\* cited by examiner

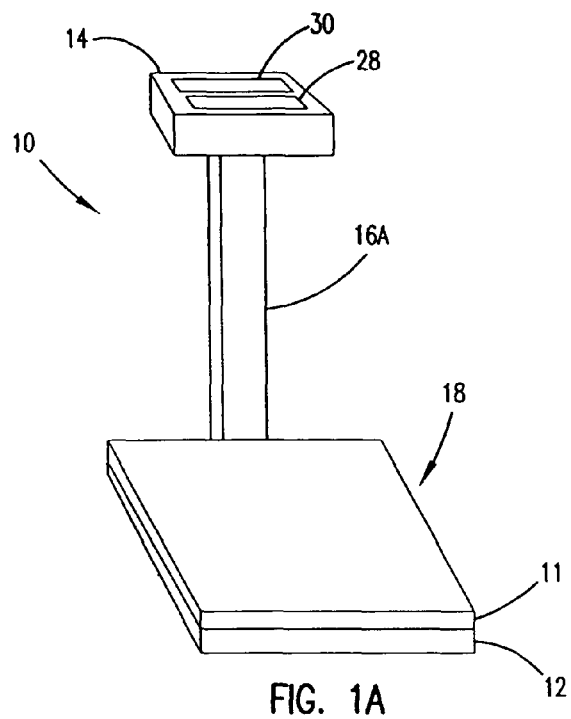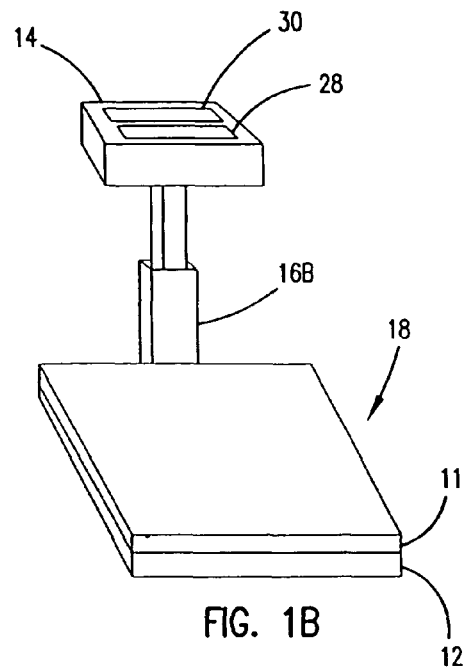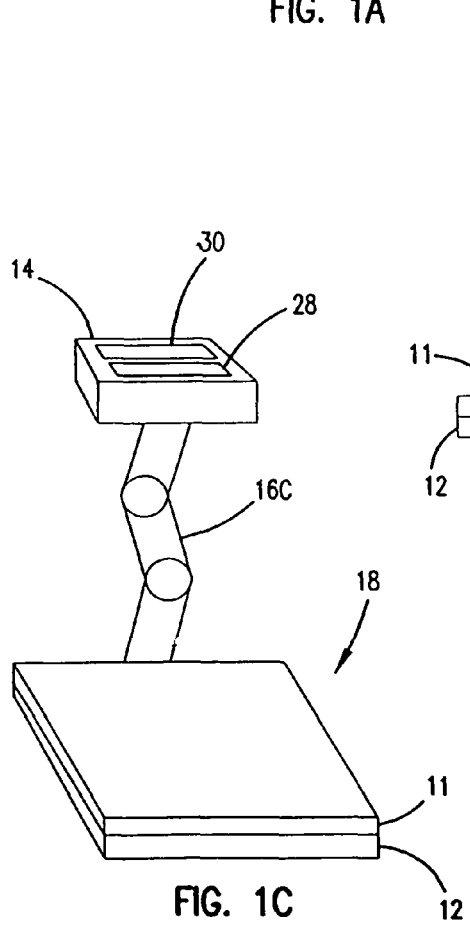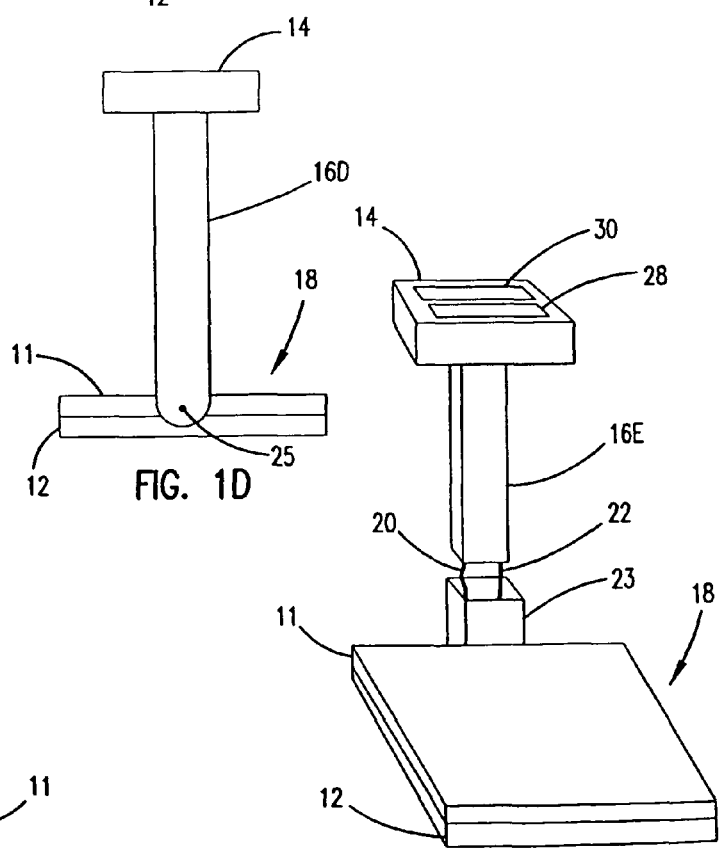
FIG. 1A
FIG. 1B
FIG. 1C
FIG. 1D
FIG. 1E

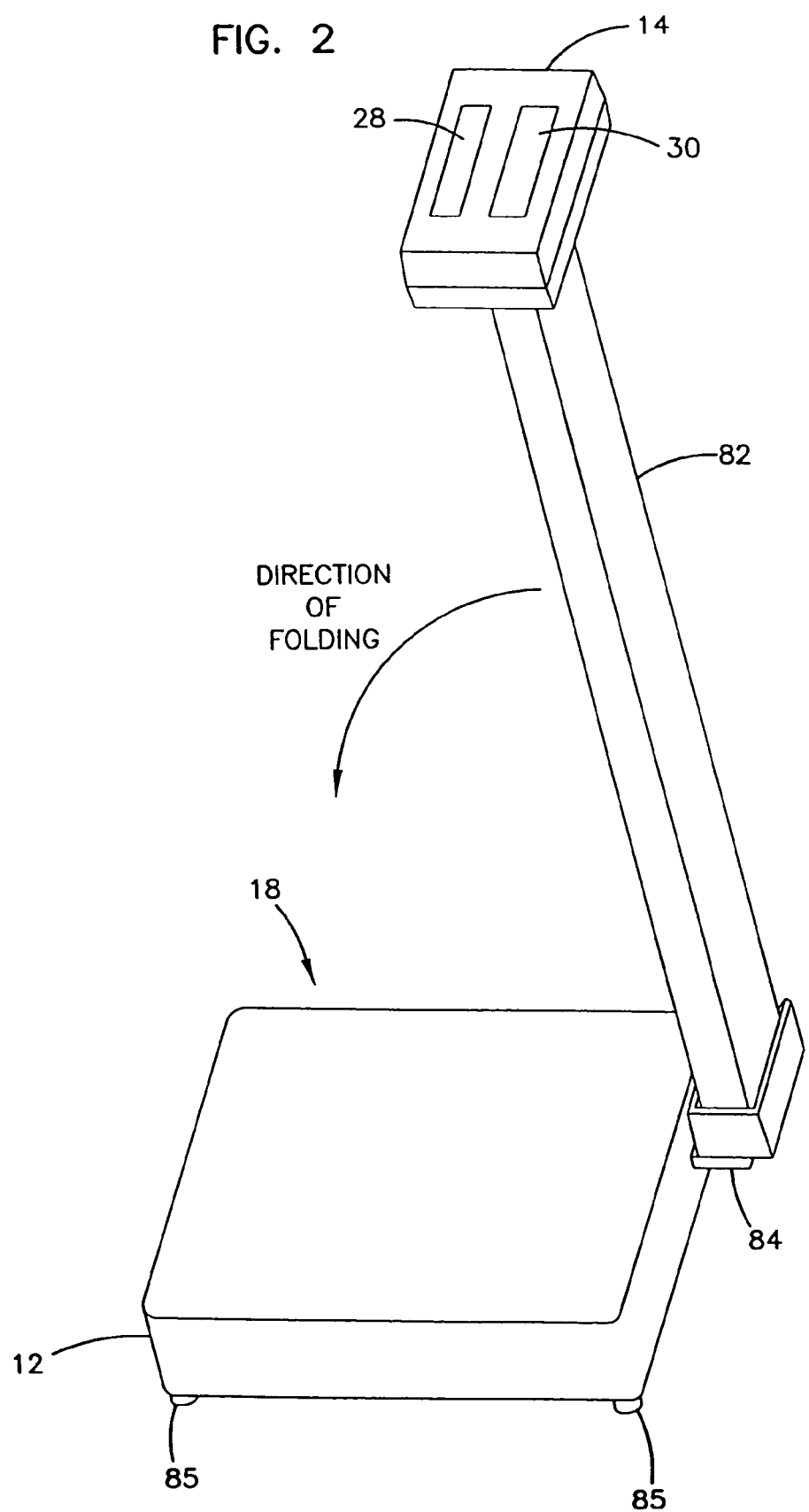

APPARATUS AND METHOD FOR MONITORING AND COMMUNICATING WELLNESS PARAMETERS OF AMBULATORY PATIENTS

CROSS-REFERENCE TO RELATED APPLICATIONS

This application is continuation of U.S. application Ser. No. 09/918,247, filed on Jul. 30, 2001, now U.S. Pat. No. 6,723,045 which is a divisional of U.S. application Ser. No. 09/293,619, filed Apr. 16, 1999, now U.S. Pat. No. 6,290,646 issued on Sep. 18, 2001, which are incorporated herein by reference.

BACKGROUND

There is a need in the medical profession for an apparatus and method capable of monitoring and transmitting physiological and wellness parameters of ambulatory patients to a remote site where a medical professional caregiver evaluates such physiological and wellness parameters. Specifically, there is a need for an interactive apparatus that is coupled to a remote computer such that a medical professional caregiver can supervise and provide medical treatment to remotely located ambulatory patients.

There is needed an apparatus that monitors and transmits physiological and wellness parameters of ambulatory patients to a remote computer, whereby a medical professional caregiver evaluates the information and provokes better overall health care and treatment for the patient. Accordingly, such an apparatus can be used to prevent unnecessary hospitalizations of such ambulatory patients.

Also, there is needed an apparatus for monitoring and transmitting such physiological and wellness parameters that is easy to use and that is integrated into a single unit. For example, there is a need for an ambulatory patient monitoring apparatus that comprises: a transducing device for providing electronic signals representative of measured physiological parameters, such as weight; an input/output device; and a communication device as a single integrated unit that offers ambulatory patients ease of use, convenience and portability.

Patients suffering from chronic diseases, such as chronic heart failure, will benefit from such home monitoring apparatus. These patients normally undergo drug therapy and lifestyle changes to manage their medical condition. In these patients, the medical professional caregiver monitors certain wellness parameters and symptoms including: weakness, fatigue, weight gain, edema, dyspnea (difficulty breathing or shortness of breath), nocturnal cough, orthopnea (inability to lie flat in bed because of shortness of breath), and paroxysmal nocturnal dyspnea (awakening short of breath relieved by sitting or standing); and body weight to measure the response of drug therapy. Patients will also benefit from daily reminders to take medications (improving compliance), reduce sodium intake and perform some type of exercise. With the information received from the monitoring device, the medical professional caregiver can determine the effectiveness of the drug therapy, the patient's condition, whether the patient's condition is improving or whether the patient requires hospitalization or an office consultation to prevent the condition from getting worse.

Accordingly, there is needed an apparatus and method for monitoring the patients from a remote location, thus allowing medical professional caregivers to receive feedback of the patient's condition without having to wait until the patient's next office visit. In addition, there is needed an apparatus and method that allows medical professional caregivers to monitor and manage the patient's condition to prevent the rehospitalization of such patient, or prevent the patient's condition from deteriorating to the point where hospitalization would be required. As such, there are social as well as economic benefits to such an apparatus and method.

The patient receives the benefits of improved health when the professional caregiver is able to monitor and quickly react to any adverse medical conditions of the patient or to any improper responses to medication. Also, society benefits because hospital resources will not be utilized unnecessarily.

As a group, patients suffering from chronic heart failure are the most costly to treat. There are approximately 5 million patients in the U.S.A. and 15 million worldwide with chronic heart failure. The mortality rate of patients over 65 years of age is 50%. Of those that seek medical help and are hospitalized, 50% are rehospitalized within 6 months. Of these, 16% will be rehospitalized twice. The patients that are hospitalized spend an average of 9.1 days in the hospital at a cost of $12,000.00 for the period. Accordingly, there is a need to reduce the rehospitalization rate of chronic heart failure patients by providing improved in-home patient monitoring, such as frequently monitoring the patient's body weight and adjusting the drug therapy accordingly.

Approximately 60 million American adults ages 20 through 74 are overweight. Obesity is a known risk factor for heart disease, high blood pressure, diabetes, gallbladder disease, arthritis, breathing problems, and some forms of cancer such as breast and colon cancer. Americans spend $33 billion dollars annually on weight-reduction products and services, including diet foods, products and programs.

There is a need in the weight management profession for an apparatus and method capable of monitoring and transmitting physiological and wellness parameters of overweight/obese patients to a remote site where a weight management professional or nutritionist evaluates such physiological and wellness parameters. Specifically, there is a need for an interactive apparatus that is coupled to a remote computer such that a weight management professional or nutritionist can supervise and provide nutritional guidance to remotely located individuals.

The apparatus allows overweight individuals to participate in a weight loss/management program with accurate weight monitoring from home. The apparatus improves the convenience for the individual participant by eliminating the need to constantly commute to the weight management center and "weigh-in." Furthermore, the individual can participate in a weight management program while under professional supervision from the privacy and comfort of their own home. Moreover, the apparatus allows the weight management professional to intervene and adapt the individuals diet and exercise routine based on the weight and wellness information received.

For the foregoing reasons, there is a need for an apparatus, system and method capable of monitoring and transmitting physiological and wellness parameters of ambulatory patients, such as body weight, to a remote location where a medical professional caregiver, weight management professional or nutritionist can evaluate and respond to the patient's medical wellness condition.

SUMMARY

The invention is directed to an apparatus, system and method that satisfies this need. The apparatus having features of the invention is capable of monitoring an ambulatory patient and establishing two way communication to a medical professional caregiver, weight management professional or nutritionist regarding the wellness parameters of such an ambulatory patient.

The apparatus comprises a physiological parameter transducing device. The device generates an electronic signal that is representative of the value of the physiological parameter being monitored. The apparatus further comprises a central processor device. The central processor device is operatively coupled to the parameter transducing device and processes the electronic signals that are representative of the physiological parameters. The apparatus further comprises an electronic receiver/transmitter communication device. The communication device having one end operatively coupled to the processor and another end operatively coupled to a communication network. The communication device is activated whenever the central processor recognizes a physiological parameter within a predetermined range. The apparatus further comprises an input device. The input device is operatively coupled to said processor and configured to receive external commands. The apparatus further comprises an output device. The output device is coupled to the processor and provides information comprising external commands, physiological symptoms, wellness parameters, and queries from the communication device. All of these devices are integrated into a single unit.

The system having features of the invention monitors an ambulatory patient and establishes communication to a caregiver, regarding the wellness parameters of such an ambulatory patient, between a first location and a remote central office location. The system comprises a monitoring apparatus located at the first location. The monitoring apparatus comprises: (a) a physiological parameter transducing device that generates an electronic signal representative of the value of the physiological parameter being monitored; (b) a central processor device that is operatively coupled to the parameter transducing device for processing the physiological parameter electronic signals; (c) an electronic receiver/transmitter communication device, said communication device having one end operatively coupled to the processor and another end operatively coupled to a communication network that is activated whenever the central processor recognizes a physiological parameter within a predetermined range; (d) an input device that is operatively coupled to the processor and configured to receive external commands; (e) an output device coupled to the processor that provides information comprising external commands, physiological symptoms, wellness parameters, and queries from the communication device, wherein these devices are integrated into a single unit. The system further comprises a processing computer at a remote central office location that is in communication with the remote monitoring apparatus and exchanges information with the monitoring apparatus.

The method having features of the invention monitors an ambulatory patient and establishes communication to a caregiver regarding the wellness parameters of such an ambulatory patient. The method comprises monitoring a physiological parameter; generating an electronic signal representative of the value of the physiological parameter; in a central processor device, processing the physiological parameter electronic signals; communicating the processed electronic signals between a first location and a remote central location; inputting external commands into the processor; and outputting the information.

BRIEF DESCRIPTION OF THE DRAWINGS

These and other features, aspects and advantages of the invention will become better understood with regard to the following description, appended claims and accompanying drawings where:

FIGS. 1A-E illustrates several embodiments of the monitoring apparatus in accordance with the invention;

FIG. 2 illustrates a monitoring apparatus with a support member in accordance with one embodiment of the invention;

DESCRIPTION

Figure 3:
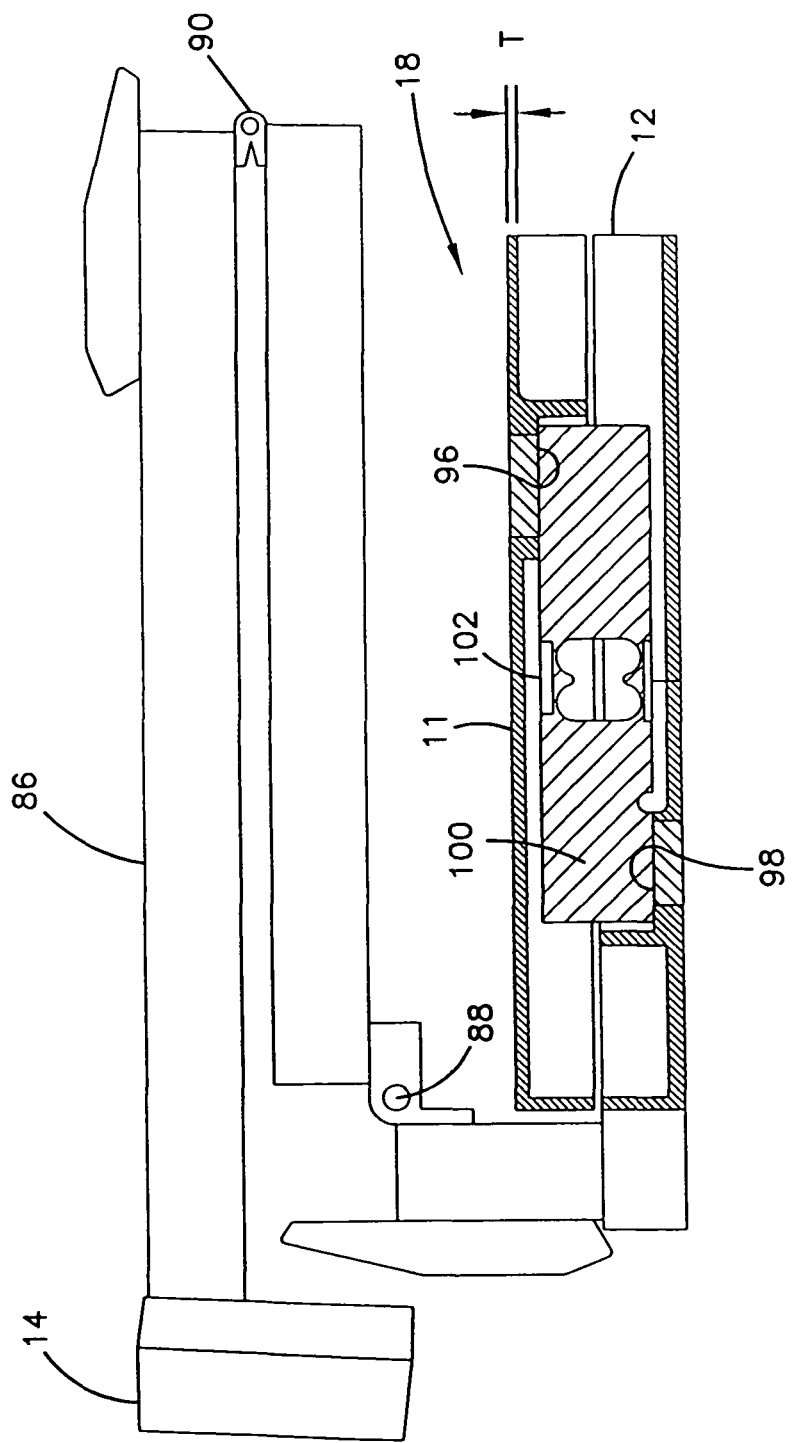
FIG. 3 illustrates a monitoring apparatus with a support member in accordance with one embodiment of the invention.

The embodiments of the invention described herein are implemented as a medical apparatus, system and method capable of monitoring wellness parameters and physiological data of ambulatory patients and transmitting such parameters and data to a remote location. At the remote location a medical professional caregiver monitors the patient's condition and provides medical treatment as may be necessary.

The monitoring device incorporates transducing devices for converting the desired measured parameters into electrical signals capable of being processed by a local computer or microprocessor system. The device interacts with the ambulatory patient and then, via an electronic communication device such as a modem, transmits the measured parameters to a computer located at a remote site. At the remote location the various indicia of the ambulatory patient's condition are monitored and analyzed by the medical professional caregiver. To provide the ambulatory patient with an added level of convenience and ease of use, such monitoring device is contained in a single integrated package.

Communication is established between the monitoring apparatus and a remote computer via modem and other electronic communication devices that are generally well known commercially available products. At the remote location, the caregiver reviews the patient's condition based on the information communicated (e.g. wellness parameters and physiological data) and provokes medical treatment in accordance with such information.

Referring now to FIG. 1A, as this embodiment of the invention is described herein, an integrated monitoring apparatus is shown generally at 10. The integrated monitoring apparatus 10 includes an electronic scale 18. The electronic scale 18 further includes a top plate 11 and a base plate 12. The integrated monitoring apparatus 10 further includes a housing 14 and a support member 16A. The base plate 12 is connected to the housing 14 through the support member 16A. The housing 14 further includes output device(s) 30 and input device(s) 28. The apparatus 10 is integrated as a single unit with the support member coupling the base plate 12 and the housing 14, thus providing a unit in a one piece construction.

It will be appreciated that other physiological transducing devices can be utilized in addition to the electronic scale 18. For example, blood pressure measurement apparatus and electrocardiogram (EKG) measurement apparatus can be utilized with the integrated monitoring apparatus 10 for recordation and/or transmission of blood pressure and EKG measurements to a remote location. It will be appreciated that other monitoring devices of physiological body functions that provide an analog or digital electronic output may be utilized with the monitoring apparatus 10.

Referring to FIGS. 1B, 1C, 1D and 1E it will be appreciated that the support member 16A (FIG. 1A) can be made adjustable. For example, FIG. 1B illustrates an embodiment of the invention utilizing a telescoping support member 16B. Likewise, FIG. 1C illustrates an embodiment of the invention utilizing a folding articulated support member 16C. FIG. 1D illustrates yet another embodiment of the invention utilizing support member 16D that folds at a pivot point 25 located at its base. It will also be appreciated that other types of articulated and folding support members may be utilized in other embodiments of the invention. For example, FIG. 1E illustrates an embodiment of the invention providing a support member 16E that is removably insertable into a socket 23. A cable 22 is passed through the support member 16E to carry electrical signals from the electronic scale 18 to the housing 14 for further processing. A tether 20 is provided to restrain the movement of the support member 16E relative to the base plate 12 once the it is removed from the socket 23.

FIG. 2 illustrates an embodiment of the invention where the support member 82 folds about pivot point 84. Folding the integrated monitoring apparatus about pivot point 84 provides a convenient method of shipping, transporting or moving the apparatus in a substantially horizontal orientation. The preferred direction of folding is indicated in the figure, however, the support member 82 can be made to fold in either direction. Furthermore, an embodiment of the invention provides rubber feet 85 underneath the base plate 12.

Furthermore, FIG. 3 illustrates one embodiment of the invention providing an articulated, folding support member 86. The support member 86 folds at two hinged pivot points 88, 90. Also illustrated is a sectional view of the scale 18, top plate 11, base plate 12, load cell 100 and strain gage 102.

Figure 4:
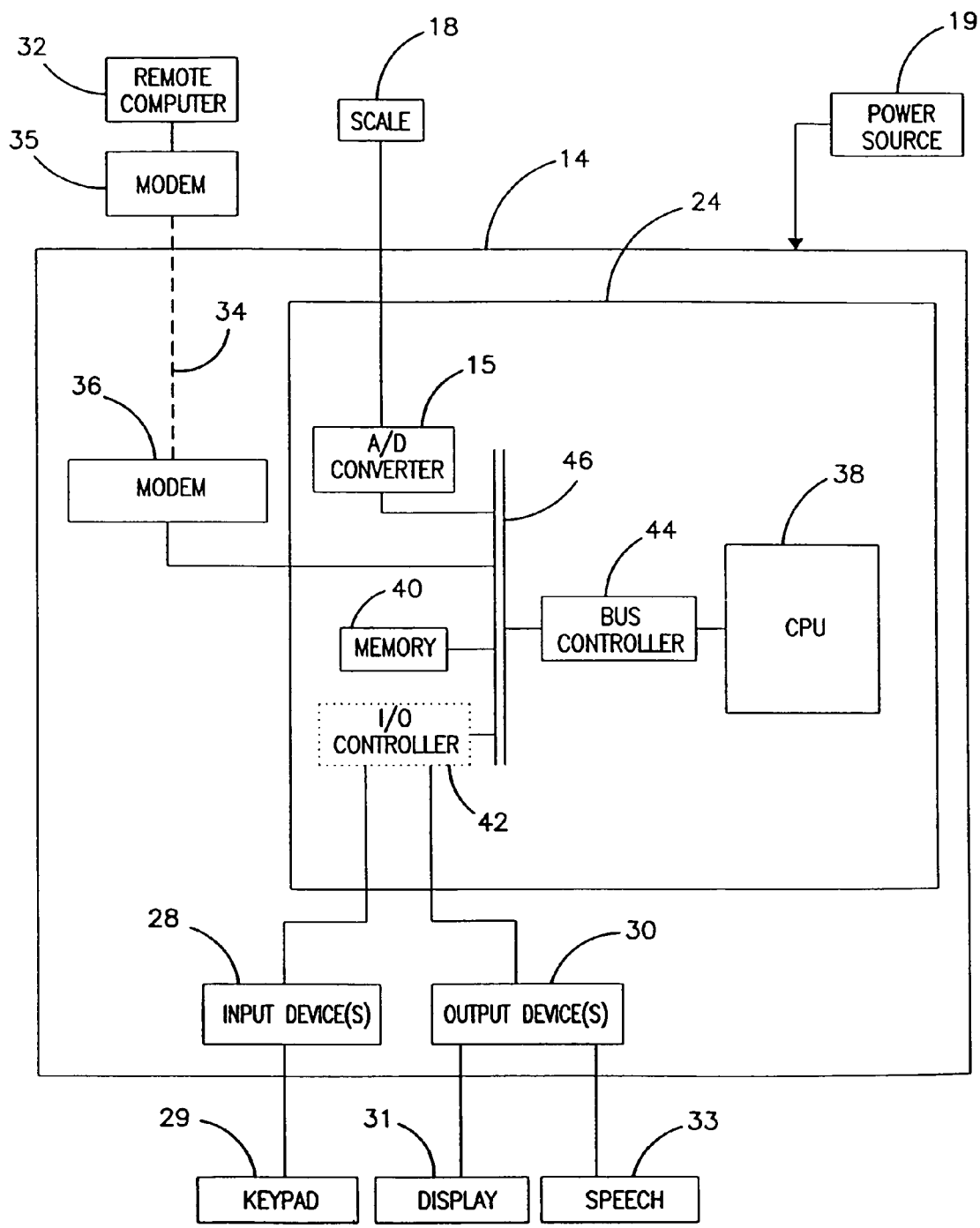
FIG. 4 is a functional block diagram of a microprocessor system forming an environment in which one embodiment of the invention may be employed.

Referring now to FIG. 4, a microprocessor system 24 including a CPU 38, a memory 40, an optional input/output (I/O) controller 42 and a bus controller 44 is illustrated. It will be appreciated that the microprocessor system 24 is available in a wide variety of configurations and is based on CPU chips such as the Intel, Motorola or Microchip PIC family of microprocessors or microcontrollers.

It will be appreciated by those skilled in the art that the monitoring apparatus requires an electrical power source 19 to operate. As such, the monitoring apparatus may be powered by: ordinary household A/C line power, DC batteries or rechargeable batteries. Power source 19 provides electrical power to the housing for operating the electronic devices. A power source for operating the electronic scale 18 is generated within the housing, however those skilled in the art will recognize that a separate power supply may be provided or the power source 19 may be adapted to provide the proper voltage or current for operating the electronic scale 18.

The housing 14 includes a microprocessor system 24, an electronic receiver/transmitter communication device such as a modem 36, an input device 28 and an output device 30. The modem 36 is operatively coupled to the microprocessor system 24 via the electronic bus 46, and to a remote computer 32 via a communication network 34 and modem 35. The communication network 34 being any communication network such as the telephone network, wide area network or Internet. It will be appreciated that the modem 36 is a generally well known commercially available product available in a variety of configurations operating at a variety of BAUD rates. In one embodiment of the invention the modem 36 is asynchronous, operates at 2400 BAUD and is readily available off-the-shelf from companies such as Rockwell or Silicon Systems Inc. (SSI).

It will be appreciated that output device(s) 30 may be interfaced with the microprocessor system 24. These output devices 30 include a visual electronic display device 31 and/or a synthetic speech device 33. Electronic display devices 31 are well known in the art and are available in a variety of technologies such as vacuum fluorescent, liquid crystal or Light Emitting Diode (LED). The patient reads alphanumeric data as it scrolls on the electronic display device 31. Output devices 30 include a synthetic speech output device 33 such as a Chipcorder manufactured by ISD (part No. 4003). Still, other output devices include pacemaker data input devices, drug infusion pumps or transformer coupled transmitters.

It will be appreciated that input device(s) 28 may be interfaced with the microprocessor system 24. In one embodiment of the invention an electronic keypad 29 is provided for the patient to enter responses into the monitoring apparatus. Patient data entered through the electronic keypad 29 may be scrolled on the electronic display 31 or played back on the synthetic speech device 33.

The microprocessor system 24 is operatively coupled to the modem 36, the input device(s) 28 and the output device(s) 30. The electronic scale 18 is operatively coupled to the central system 24. Electronic measurement signals from the electronic scale 18 are processed by the A/D converter 15. This digitized representation of the measured signal is then interfaced to the CPU 38 via the electronic bus 46 and the bus controller 44. In one embodiment of the invention, the physiological transducing device includes the electronic scale 18. The electronic scale 18 is generally well known and commercially available. The electronic scale 18 may include one or more of the following elements: load cells, pressure transducers, linear variable differential transformers (LVDTs), capacitance coupled sensors, strain gages and semiconductor strain gages. These devices convert the patient's weight into a useable electronic signal that is representative of the patient's weight.

In will be appreciated that Analog-to-Digital (A/D) converters are also generally well known and commercially available in a variety of configurations. Furthermore, an A/D converter 15 may be included within the physiological transducing device or within the microprocessor system 24 or within the housing 14. One skilled in the art would have a variety of design choices in interfacing a transducing device comprising an electronic sensor or transducer with the microprocessor system 24.

The scale 18 may provide an analog or digital electronic signal output depending on the particular type chosen. If the electronic scale 18 provides an analog output signal in response to a weight input, the analog signal is converted to a digital signal via the A/D converter 15. The digital signal is then interfaced with the electronic bus 46 and the CPU 38. If the electronic scale 18 provides a digital output signal in response to a weight input, the digital signal may be interfaced with electronic bus 46 and the CPU 38.

Figure 5:
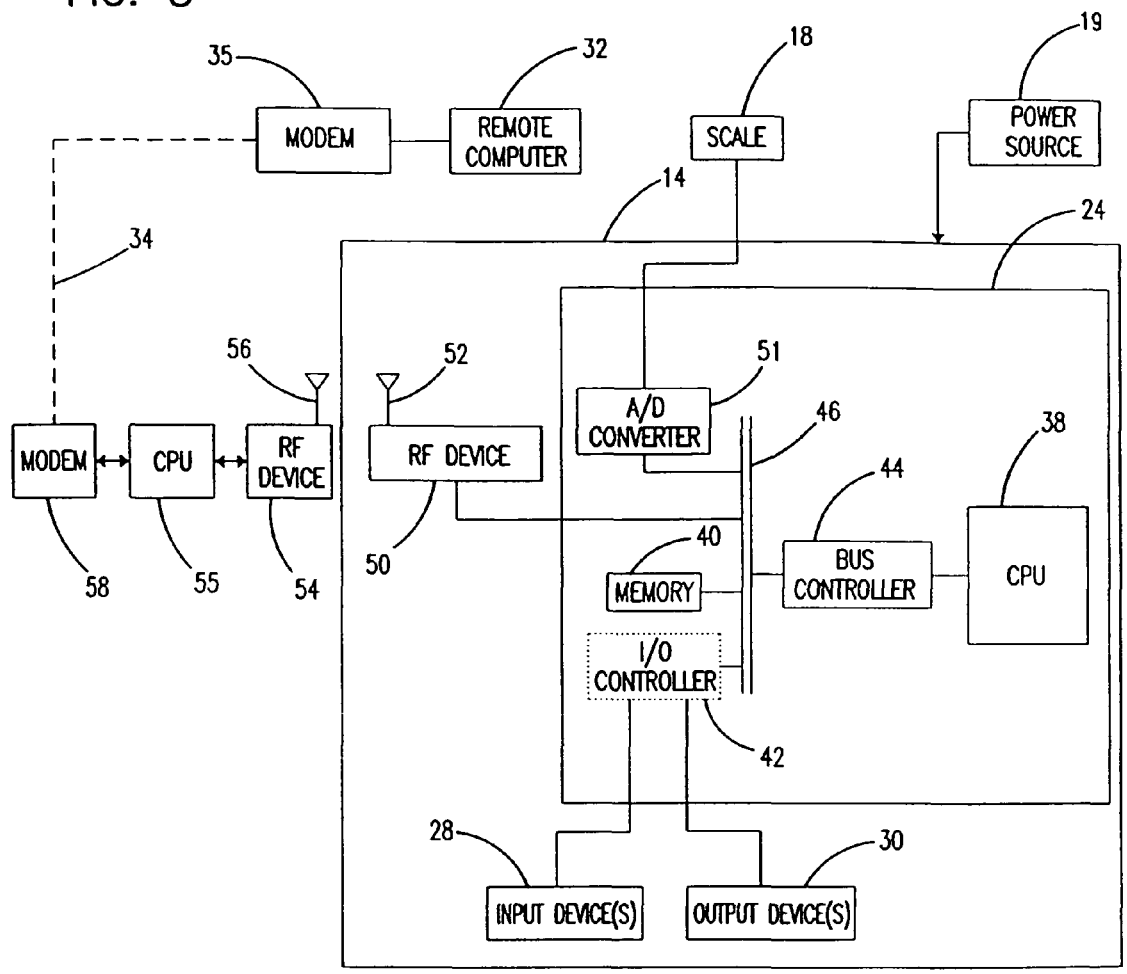
FIG. 5 is functional block diagram of a microprocessor system forming the environment in which one embodiment of the invention may be employed.

FIG. 5 illustrates one embodiment of the invention where the communication device is a radio frequency (RF) transceiver. The transceiver comprises a first radio frequency device 50 including an antenna 52, and a second radio frequency device 54, including an antenna 56. The first radio frequency device 52 is operatively coupled to the microprocessor system 24 via the electronic bus 46, and is in radio communication with the second radio frequency device 54. The second radio frequency device 54 is operatively coupled through a microprocessor 55 which is operatively coupled to a modem 58. The modem 58 is coupled to the communication network 34 and is in communication with the remote computer 32 via the modem 35. The first radio frequency device 50 and the second radio frequency device 54 are remotely located, one from the other. It will be appreciated that such radio frequency devices 50, 54 are generally well known and are commercially available products from RF Monolithics Inc. (RFM).

In one embodiment of the invention, such transceivers operate at radio frequencies in the range of 900-2400 MHz. Information from the microprocessor system 24 is encoded and modulated by the first RF device 50 for subsequent transmission to the second RF device 54, located remotely therefrom. The second RF device 54 is coupled to a conventional modem 58 via the microprocessor 55. The modem 58 is coupled to the communication network 34 via a in-house wiring connection and ultimately to the modem 35 coupled to the remote computer 32. Accordingly, information may be transmitted to and from the microprocessor system 24 via the RF devices 50, 54 via a radio wave or radio frequency link, thus providing added portability and flexibility to the monitoring apparatus 10. It will be appreciated that various other communications devices may be utilized such as RS-232 serial communication connections, Internet communications connection as well as satellite communication connections. Other communications devices that operate by transmitting and receiving infra-red (IR) energy can be utilized to provide a wireless communication link between the patient monitoring apparatus 10 and a conveniently located network connection. Furthermore, X-10™ type devices can also be used as part of a communication link between the patient monitoring apparatus 10 and a convenient network connection in the home. X-10 USA and other companies manufacture a variety of devices that transmit/receive data without the need for any special wiring. The devices works by sending signals through the home's regular electrical wires using what is called power line carrier (PLC).

Figure 6:
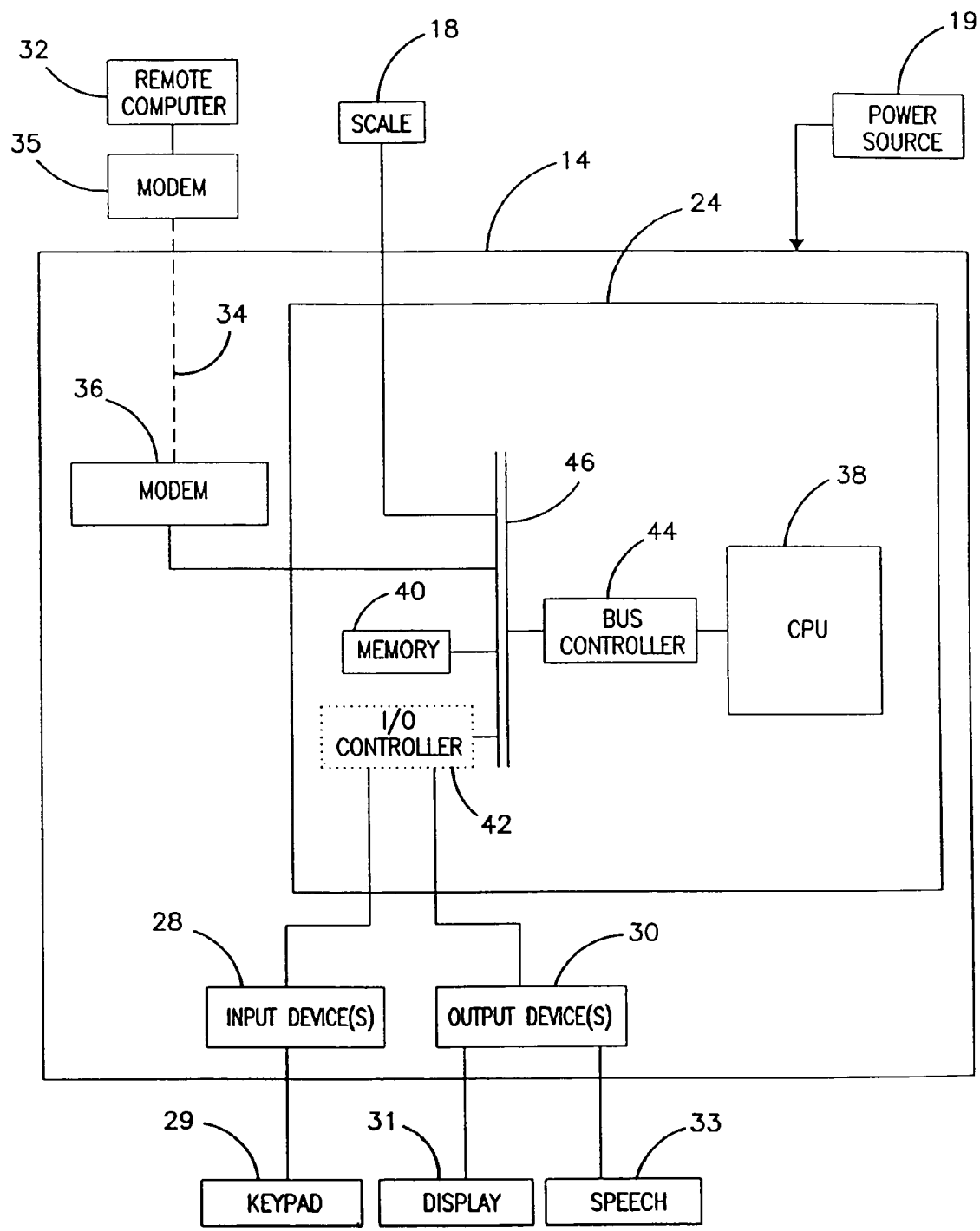
FIG. 6 is a functional block diagram of a microprocessor system forming the environment in which one embodiment of the invention may be employed.

Referring now to FIG. 6, one embodiment of the invention wherein a digital electronic scale 21 is provided. Digital weight measurements from the digital electronic scale 21 may be interfaced with the microprocessor system and CPU 38 without requiring additional amplification, signal conditioning and A/D converters.

Figure 7:
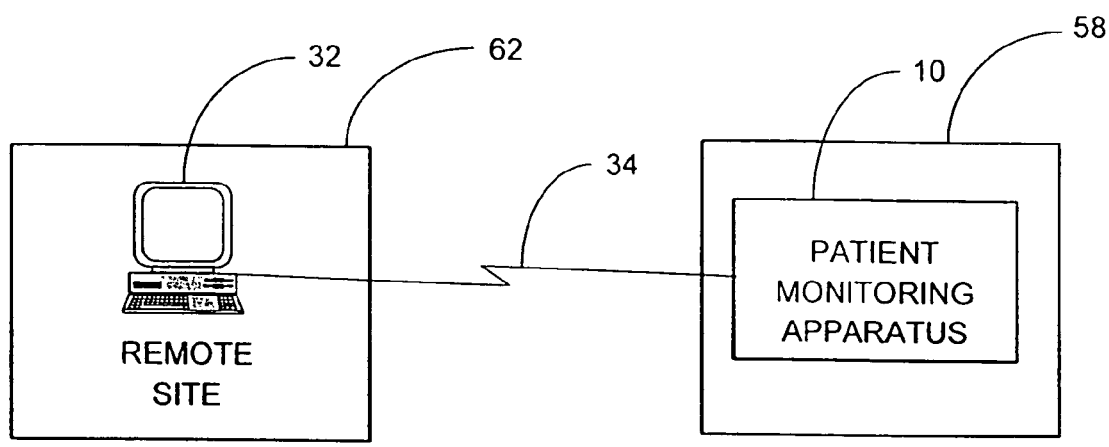
FIG. 7 illustrates a system in which one embodiment of the invention may be employed.

Referring now to FIG. 7, a two way communication system in accordance with the principals of the present invention is shown. The physiological data of an ambulatory patient is monitored utilizing monitoring apparatus 10 at a local site 58 and is transmitted to a remote computer 32 located at a remote computer site 62 via communication network 34. At the remote computer site 62 a medical professional caregiver such as a nurse, physician or nurse practitioner monitors the patient data and provokes treatment in accordance with such data.

Figure 8:
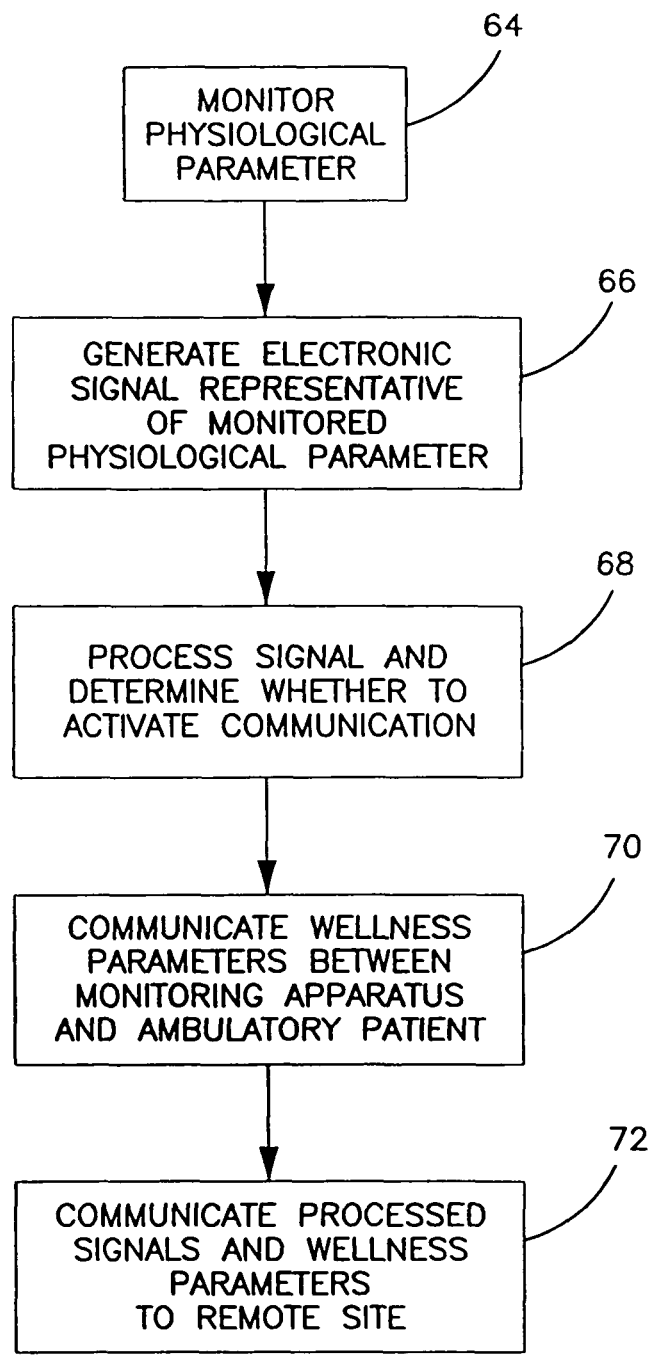
FIG. 8 is a logic flow diagram illustrating the steps utilized to implement one embodiment of the invention.

Operations to perform the preferred embodiment of the invention are shown in FIG. 8. Block 64 illustrates the operation of monitoring or measuring the ambulatory patient's physiological parameter. In one embodiment of the invention, namely for chronic heart failure patients, the physiological parameter monitored is the patient's weight. However, it will be appreciated by those skilled in the art that the physiological parameters may include blood pressure, EKG, temperature, urine output and any other.

Block 66 illustrates the operation of converting a monitored or measured physiological parameter from a mechanical input to an electronic output by utilizing a transducing device. In one embodiment of the invention the transducing device is an electronic scale 18, which converts the patient's weight into a useable electronic signal.

At block 68, the microprocessor system 24 processes the electronic signal representative of the transduced physiological parameter. If the resulting parameter value is within certain preprogrammed limits the microprocessor system 24 initiates communication within the remote computer 32 via the communication device 36 over the communication network 34.

Block 70 illustrates the operation whereby information such as wellness parameters and physiological data are communicated between the monitoring apparatus 10 and the ambulatory patient. An exemplary list of the questions asked to the patient by the monitoring apparatus are provided in Table 5.

Referring now to FIGS. 7 and 8, upon establishing communication between the local monitoring apparatus 10, at the local site 58, and the remote computer 32, at remote site 62, block 72 illustrates the operation of communicating or transmitting processed signals representative of physiological data and wellness parameters from the local site 58 to the remote site 62.

Figure 9:
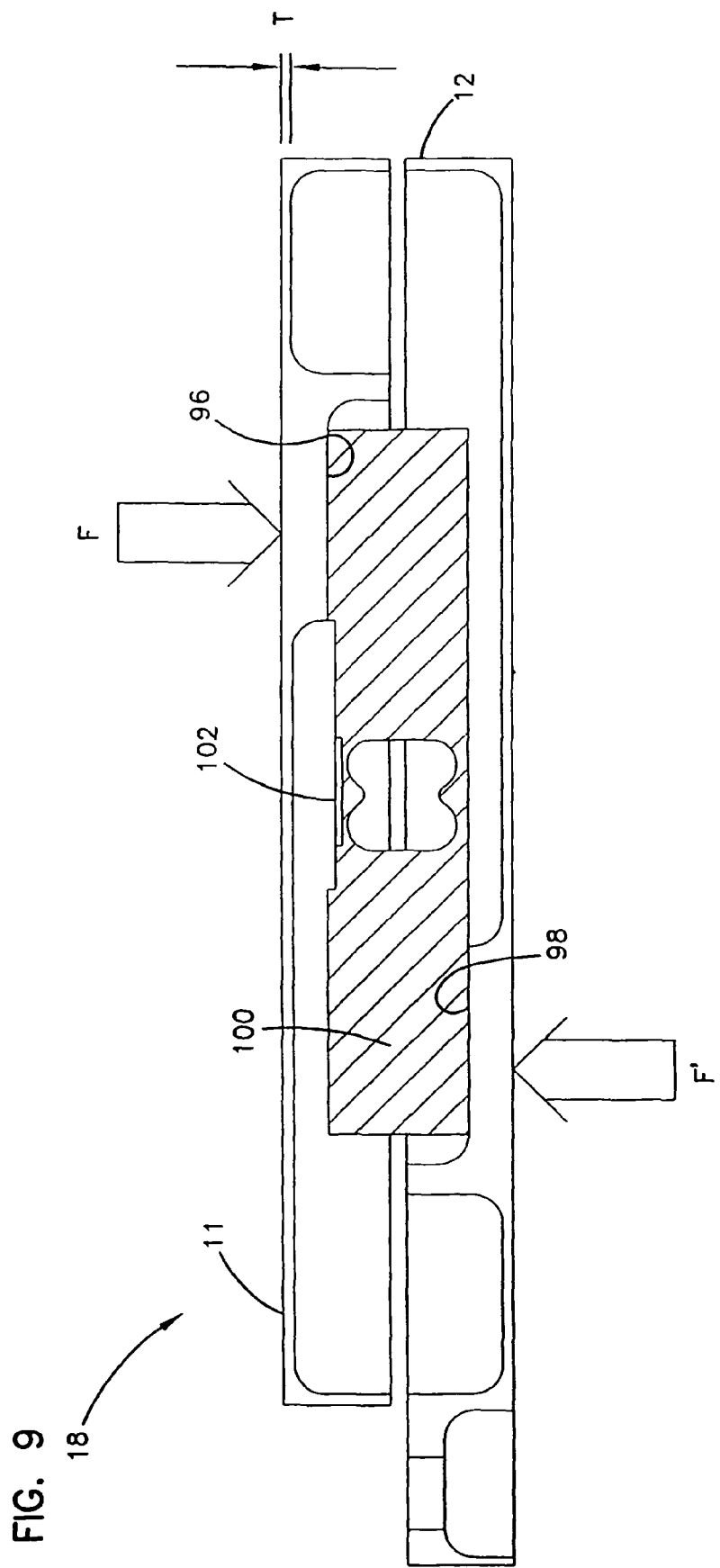
FIG. 9 illustrates a sectional view of the electronic scale in accordance with one embodiment of the invention.

FIG. 9 is a sectional view the scale 18 portion of one embodiment of the invention. The scale 18 comprises a top plate 11 and a base plate 12. The top plate 11 and the base plate 12 having a thickness "T". A load cell 100 is disposed between the top plate 11 and the base plate 12 and rests on support/mounting surfaces 96 and 98.

The load cell 100 is a transducer that responds to a forces applied to it. During operation, when a patient steps on the electronic scale 18, the load cell 100 responds to a force "F" transmitted through the top plate 11 and a first support/mounting surface 96. The support/mounting surface 96 is contact with a first end on a top side of the load cell 100. A force "F'" that is equal and opposite to "F" is transmitted from the surface that the electronic scale 18 is resting on, thorough the base plate 12 and a second support/mounting surface 98. The second support/mounting surface 98 is in contact with a second end on a bottom side of the load cell 100. In one embodiment, the load cell 100 is attached to the top plate 11 and the base plate 12, respectively, with bolts that engage threaded holes provided in the load cell 100. In one embodiment the load cell 100 further comprises a strain gage 102.

The strain gage 102 made from ultra-thin heat-treated metallic foils. The strain gage 102 changes electrical resistance when it is stressed, e.g. placed in tension or compression. The strain gage 102 is mounted or cemented to the load cell 100 using generally known techniques in the art, for example with specially formulated adhesives, urethanes, epoxies or rubber latex. The positioning of the strain gage 102 will generally have some measurable effect on overall performance of the load cell 100. Furthermore, it will be appreciated by those skilled in the art that additional reference strain gages may be disposed on the load cell where they will not be subjected to stresses or loads for purposes of temperature compensating the strain gage 102 under load. During operation over varying ambient temperatures, signals from the reference strain gages may be added or subtracted to the measurement signal of the strain gage 102 under load to compensate for any adverse effects of ambient temperature on the accuracy of the strain gage 102.

The forces, "F" and "F'", apply stress to the surface on which the strain gage 102 is attached. The weight of the patient applies a load on the top plate 11. Under the load the strain gage(s) 102 mounted to the top of the load cell 100 will be in tension/compression as the load cell bends. As the strain gage 102 is stretched or compressed its resistance changes proportionally to the applied load. The strain gage 102 is electrically connected such that when an input voltage or current is applied to the strain gage 102, an output current or voltage signal is generated which is proportional to the force applied to the load cell 100. This output signal is then converted to a digital signal by A/D converter 15.

Figure 10:
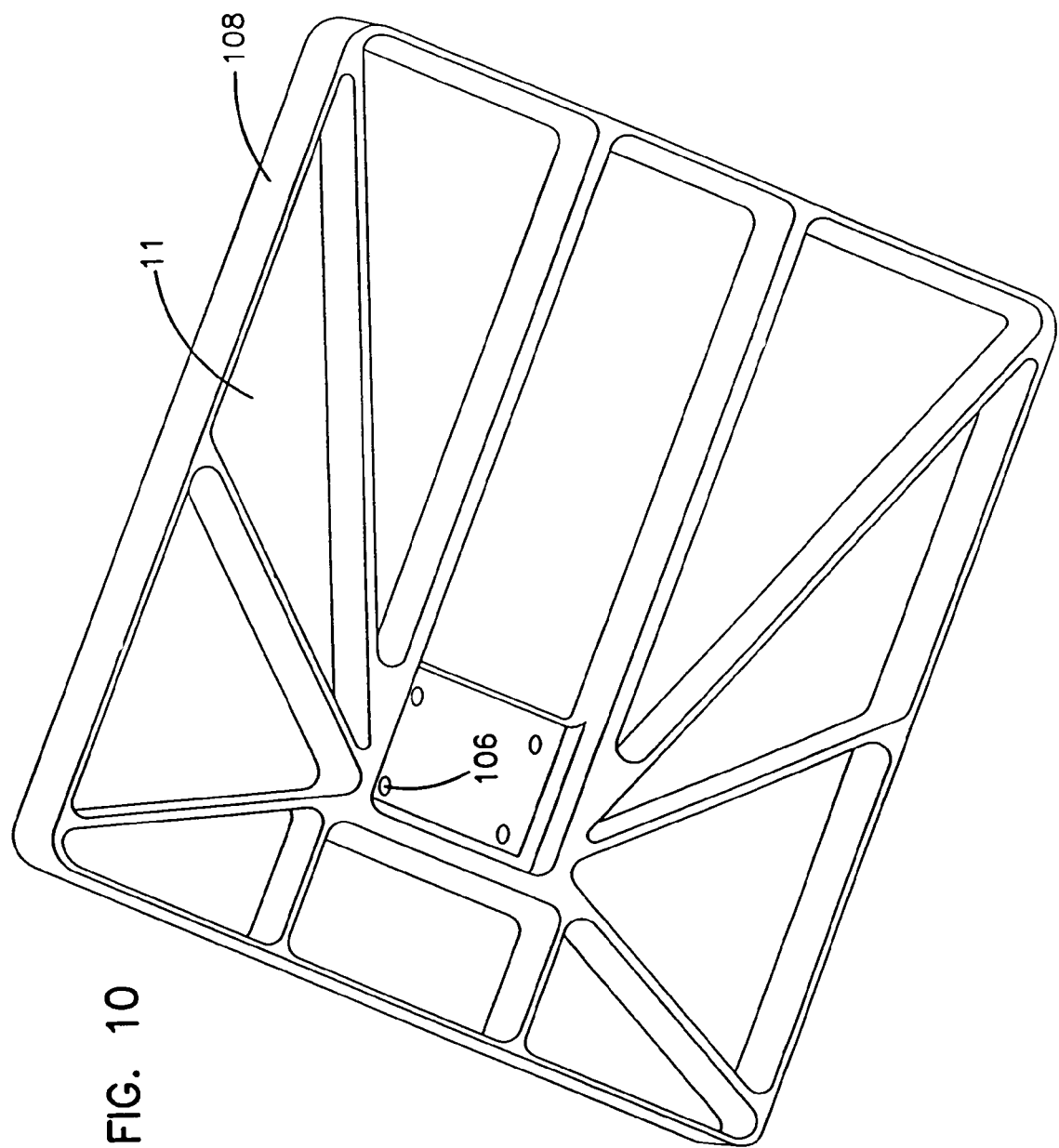
FIG. 10 illustrates a top plate of the electronic scale in accordance with one embodiment of the invention.

The design of the load cell 100 having a first end on a top side attached to the top plate 11 and a second end on a bottom side attached to the base plate 12 provides a structure for stressing the strain gage 102 in a repeatable manner. The structure enables a more accurate and repeatable weight measurement. This weight measurement is repeatable whether the scale 18 rests on a rigid tile floor or on a carpeted floor. FIG. 10 illustrates one embodiment of the top plate 11 that provides four mounting holes 106 for attaching the base plate 12 to one end of the load cell 100. The base plate 12 provides similar holes for attaching to the other end of the load cell 100. The top plate 11 and the base plate 12 (not shown) each comprise a plurality of stiffening ribs 108 that add strength and rigidity to the electronic scale 18.

Table 1 shows multiple comparative weight measurements taken with the electronic scale 18 resting on a tile floor and a carpeted floor without rubber feet on the scale 18. The measurements were taken using the same load cell 100. The thickness "T" of the top plate 11 and supporting ribs was 0.125" except around the load cell, where the thickness of the supporting ribs was 0.250". The thickness of the load cell 100 support/mounting surfaces 96, 98 (FIG. 9) was 0.375". As indicated in Table 1, with the scale 18 resting on a tile floor, the average measured weight was 146.77 lbs., with a standard deviation of 0.11595. Subsequently, with the scale 18 resting on a 0.5" carpet with 0.38" pad underneath and an additional 0.5" rug on top of the carpet, the average measured weight was 146.72 lbs., with a standard deviation of 0.16866.

TABLE 1

Thick Scale Parts Around Load Cell 0.250"

| TILE (lbs.) | CARPET (lbs.) |
|---|---|
| 146.9 | 146.7 |
| 146.7 | 147 |
| 146.9 | 146.6 |
| 146.8 | 146.7 |
| 146.6 | 146.6 |
| 146.8 | 147 |
| 146.8 | 146.5 |
| 146.7 | 146.6 |
| 146.9 | 146.8 |
| 146.6 | 146.7 |
| 0.11595 (stddev) | 0.16866 (stddev) |
| 146.77 (average) | 146.72 (average) |

Table 2 shows multiple weight measurements taken with the scale 18 on a tile floor and a carpeted floor with rubber feet on the bottom of the scale 18. The measurements were taken using the same load cell 100. The thickness "T" of the top plate 11 was 0.125" including the thickness around the load cell. As indicated in Table 2, with the scale 18 resting on a tile floor on rubber feet, the average measured weight was 146.62 lbs., with a standard deviation of 0.07888. Subsequently, with the scale 18 resting on a 0.5" carpet with 0.38" pad underneath and an additional 0.5" rug on top of the carpet, the average measured weight was 146.62 lbs., with a standard deviation of 0.04216.

TABLE 2

Thin Scale Parts Throughout 0.125"

| TILE (lbs.) | CARPET (lbs.) |
|---|---|
| 146.7 | 146.7 |
| 146.7 | 146.7 |
| 146.6 | 146.6 |
| 146.6 | 146.6 |
| 146.6 | 146.6 |
| 146.6 | 146.6 |
| 146.5 | 146.6 |
| 146.7 | 146.6 |
| 146.5 | 146.6 |
| 146.7 | 146.6 |
| 0.07888 (stddev) | 0.04216 (stddev) |
| 146.62 (average) | 146.62 (average) |

Table 3 shows multiple weight measurements taken with an off-the-shelf conventional electronic scale. As indicated in table 3, with the off-the-shelf conventional scale resting on the tile floor, the average measured weight was 165.5571 lbs., with a standard deviation of 0.20702. Subsequently, with the off-the-shelf conventional scale resting on a 0.5" carpet with 0.38" pad underneath and an additional 0.5" rug on top of the carpet, the average measured weight was 163.5143 lbs., with a standard deviation of 0.13093.

TABLE 3

Off-The-Shelf Conventional Scale

| TILE (lbs.) | CARPET (lbs.) |
|---|---|
| 165.9 | 163.5 |
| 165.5 | 163.4 |
| 165.8 | 163.7 |
| 165.4 | 163.6 |
| 165.5 | 163.6 |
| 165.4 | 163.5 |
| 165.4 | 163.3 |
| — | 163.4 |
| 0.20702 (stddev) | 0.13093 (stddev) |
| 165.5571 (average) | 163.5143 (average) |
| 2.042857 (% of difference) | 1.249345 (% of difference) |

The summary in Table 4 is a comparative illustration of the relative repeatability of each scale while resting either on a tile floor or on a carpeted floor.

TABLE 4

SUMMARY OF DATA:

| TRIAL | TILE | STDDEV | CARPET | STDDEV | TILE VS. CARPET |
|---|---|---|---|---|---|
| Heavy Scale Parts All 0.125" Except Cell Around the Load Cell 0.250" | | | | | |
| 1 | 146.77 | 0.1159 | 146.72 | 0.1686 | 0.05 |
| 2 | 146.67 | 0.0823 | 146.72 | 0.1906 | 0.05 |
| Thin Scale Parts All 0.125" | | | | | |
| 1 | 146.62 | 0.0788 | 146.62 | 0.04216 | 0.00 |
| Off-The-Shelf Conventional Scale | | | | | |
| 1 | 165.55 | 0.207 | 163.51 | 0.1309 | 2.04 |

The foregoing description was intended to provide a general description of the overall structure of several embodiments of the invention, along with a brief discussion of the specific components of these embodiments of the invention. In operating the apparatus 10, an ambulatory patient utilizes the monitoring apparatus 10 to obtain a measurement of a particular physiological parameter. For example, an ambulatory patient suffering from chronic heart failure will generally be required to monitor his or her weight as part of in-home patient managing system. Accordingly, the patient measures his or her weight by stepping onto the electronic scale 18, integrally located within the base plate 12 of the monitoring apparatus 10.

Referring now to FIG. 4, the modem 36 of the monitoring apparatus 10 will only activate if the measured weight is within a defined range such as +/−10 lbs, +/−10% or any selected predetermined value of a previous weight measurement. The patient's previous symptom free weight (dry weight) is stored in the memory 40. The dry weight is the patient's weight whenever diuretics are properly adjusted for the patient, for example. This prevents false activation of the modem 36 if a child, pet, or other person accidentally steps onto the electronic scale 18.

Upon measuring the weight, the microprocessor system 24 determines whether it is within a defined, required range such as +/−10 lbs. or +/−10% of a previously recorded weight stored in memory 40. The monitoring apparatus 10 then initiates a call via the modem 36 to the remote site 62. Communications is established between the local monitoring apparatus 10 and the remote computer 32. In one embodiment of the invention, the patient's weight is electronically transferred from the monitoring apparatus 10 at the local site 58 to the remote computer 32 at the remote site 62. At the remote site 62 the computer program compares the patient's weight with the dry weight and wellness information and updates various user screens. The program can also analyze the patient's weight trend over the previous 1-21 days. If significant symptoms and/or excessive weight changes are reported, the system alerts the medical care provider who may provoke a change to the patient's medication dosage, or establish further communication with the patient such as placing a telephone to the patient. The communication between the patient's location and the remote location may be one way or two way communication depending on the particular situation.

To establish the patient's overall condition, the patient is prompted via the output device(s) 30 to answer questions regarding various wellness parameters. An exemplary list of questions, symptoms monitored and the related numerical score is provided in Table 5 as follows:

TABLE 5

Health Check Score

| Question | Symptom | Value |
| --- | --- | --- |
| Above Dry Weight? | Fluid accumulation | 10 |
| Are you feeling short of breath? | Dyspnea | 10 |
| Did you awaken during the night short of breath? | Paroxysmal nocturnal dyspnea | 5 |
| Did you need extra pillows last night? | Congestion in the lungs | 5 |
| Are you coughing more than usual? | Congestion in the lungs | 3 |
| Are your ankles or feet swollen? | Pedal edema | 5 |
| Does your stomach feel bloated? | Stomach edema | 3 |
| Do you feel dizzy or lightheaded? | Hypotension | 5 |
| Are you more tired than usual? | Fatigue | 2 |
| Are you taking your medication? | Medication compliance | 7 |
| Has your appetite decreased? | Appetite | 2 |
| Are you reducing your salt intake? | Sodium intake | 1 |
| Did you exercise today? | Fitness | 1 |

At the remote site 62 the medical professional caregiver evaluates the overall score according to the wellness parameter interrogation responses (as shown in Table 5). For example, if the patient's total score is equal to or greater than 10, an exception is issued and will either prompt an intervention by the medical professional caregiver in administering medication, or prompt taking further action in the medical care of the patient.

The output device(s) 30 varies based on the embodiment of the invention. For example, the output device may be a synthetic speech generator 33. As such, the wellness parameters are communicated to the patient via the electronic synthetic speech generator 33 in the form of audible speech. It will be appreciated that electronic speech synthesizers are generally well known and widely available. The speech synthesizer converts electronic data to an understandable audible speech.

Accordingly, the patient responds by entering either "YES" or "NO" responses into the input device 28, which may include for example, an electronic keypad 29. However, in one embodiment of the invention, the input device may also include a generic speech recognition device such as those made by International Business Machines (IBM), Dragon Systems, Inc. and other providers. Accordingly, the patient replies to the interrogations merely by speaking either "YES" or "NO" responses into the speech recognition input device.

In embodiments of the invention that include electronic display 31 as an output device 30, the interrogations as well as the responses are displayed and/or scrolled across the display for the patient to read. Generally, the electronic display will be positioned such that it is viewable by the patient during the information exchanging process between the patient and the remote computer 32.

Upon uploading the information to the remote computer 32, the medical professional caregiver may telephone the patient to discuss, clarify or validate any particular wellness parameter or physiological data point. Furthermore, the medical professional caregiver may update the list of wellness parameter questions listed in Table 5 from the remote site 62 over the two way communication network 34. Modifications are transmitted from the remote computer 32 via modem 35, over the communication network 34, through modem 36 and to the monitoring apparatus 10. The modified query list is then stored in the memory 40 of the microprocessor system 24.

Thus, it will be appreciated that the previously described versions of invention provide many advantages, including addressing the needs in the medical profession for an apparatus and method capable of monitoring and transmitting physiological and wellness parameters of ambulatory patients to a remote site whereby a medical professional caregiver can evaluate such physiological and wellness parameters and make decisions regarding the patient's treatment.

Also, it will be appreciated that the previously described versions of invention provide other advantages, including addressing the need for an apparatus for monitoring and The claimed invention is:

1. A system for monitoring a patient with a previously diagnosed chronic condition and establishing communication with a device located in a remote location, the system transferring information from a first location to the remote location, the system comprising:
   (a) a portable monitoring apparatus at the first location comprising:
      a transducing device that generates an electronic signal representative of a physiological parameter of the patient;
      a processor operatively coupled to the transducing device and programmed to process the electronic signal from the transducing device;
      a communication device operatively coupled to the processor and to a communication network;
      an output device operatively coupled to the processor, the output device being configured to present questions to the patient that establish whether the patient is perceiving symptoms related to the previously diagnosed chronic condition;
      an input device operatively coupled to the processor to receive answers from the patient in response to the questions, wherein the answers include at least yes and no answers; and
   (a) a processing computer at the remote location, the processing computer communicatively coupled to the monitoring apparatus,
      wherein the processing computer receives the processed electronic signal to generate physiological data, and also receives an indication of each of the answers, to generate symptom data,
      wherein the processing computer analyzes a trend of the physiological data and an overall symptom data score, wherein the overall symptom data score is generated based on pre-assigned score values associated with each of the answers, and if the physiological data trend and the overall symptom data score exceeds an expected change over time, then the processing computer issues an alert, wherein the pre-assigned score values include at least numerical score values.

2. The system of claim 1, wherein the monitoring apparatus comprises:
   a base, the base including the transducing device;
   a housing, the housing including the processor, the communication device, the input device, and the output device; and
   a support member extending between the base and the housing.

3. The system of claim 1, wherein the communication device is a modem.

4. The system of claim 1, wherein the communication between the monitoring apparatus and processing computer occurs via an RS-232 port.

5. The system of claim 1, wherein the communication between the monitoring apparatus and the processing computer occurs via the Internet.

6. The system of claim 1, wherein the monitoring apparatus comprises a second output device controlled by the processor that is arranged to infuse a drug into the patient.

7. The system of claim 1, wherein the communication device is selected from a group consisting of: a satellite communication device and an infrared communication device.

8. The system of claim 1, wherein the communication device is a Radio Frequency (RF) transceiver.

9. The system of claim 8, wherein the RF transceiver has two portions, the first portion being operatively coupled to the processor and in communication with the second portion, the second portion being located remotely from the first portion and operatively coupled to the communication network.

10. The system according to claim 9, wherein the second portion of the RF transceiver includes a wall mounting mechanism.

11. The system of claim 1, wherein a nurse is in communication with the patient through the communication network.

12. The system of claim 1, wherein the output device is a synthetic speech communication device arranged to audibly communicate information to the patient.

13. The system of claim 1, wherein the output device is a visual display device.

14. A method for monitoring a patient, with a previously diagnosed chronic condition comprising:
   measuring, with a transducing device, an electronic signal representative of a physiological parameter of the patient;
   processing the electronic signal with a processor operatively coupled to the transducing device;
   presenting, with an output device operatively coupled to the processor, questions to the patient related to whether the patient is perceiving symptoms related to the previously diagnosed chronic condition;
   receiving, in response to the questions, answers from the patient with an input device operatively coupled to the processor, the answers including yes and no answers;
   communicating the answers and the the processed electronic signal to a remote processing computer with a communication device operatively coupled to the processor and to a communication network;
   receiving, at the remote processing computer, the processed electronic signal, thereby providing a source of physiological data, and also receiving the answers, thereby providing a source of symptom data;
   generating an overall score based on at least one of the physiological data and the symptom data;
   analyzing, at the remote processing computer, a trend of the physiological data over time and the overall score; and
   if at least one of the physiological data trend over time exceeds an expected change over time and the overall score exceeds a threshold, then issuing an alert.

15. The method of claim 14, wherein the communicating step is accomplished via a modem.

16. The method of claim 14, wherein the communicating step is accomplished via an RS-232 port.

17. The method of claim 14, wherein the communicating step is accomplished via the Internet.

18. The method of claim 14, wherein the communicating step is accomplished via an infrared communication device.

19. The method of claim 14, wherein the communicating step is accomplished via a satellite communication device.

20. The method of claim 14, wherein the communicating step is accomplished via a Radio Frequency (RF) transceiver.

21. The method of claim 20, wherein a first portion of the RF transceiver is operatively coupled to the processor and communicates with a second portion of the RF transceiver, and wherein the second portion is located remotely from the first portion and is operatively coupled to the communication network.

22. The method of claim 14, wherein the presenting step is accomplished via a synthetic speech communication device arranged to audibly communicate information to the patient.

23. The method of claim 14, wherein the presenting step is accomplished via a visual display device.

24. A system for monitoring a patient, with a previously diagnosed chronic condition comprising:
(a) a monitoring apparatus at the first location comprising:
a transducing device that generates an electronic signal representative of a physiological parameter of the patient;
a processor operatively coupled to the transducing device and programmed to process the electronic signal from the transducing device;
a communication device operatively coupled to the processor and to a communication network;
an output device operatively coupled to the processor, the output device being configured to present questions to the patient that establish whether the patient is perceiving symptoms related to the previously diagnosed chronic condition;
an input device operatively coupled to the processor, the input device being configured to receive answers from the patient in response to the questions, each of the answers having a pre-assigned numerical score value; and
(b) a processing computer at the remote office location, the processing computer communicatively coupled to the monitoring apparatus,
wherein the processing computer receives the processed electronic signal, thereby providing a source of physiological data, and also receives the answers, and
wherein the processing computer analyzes physiological data trend over time and a sum of the pre-assigned numerical score values associated with each of the answers; and
if the physiological data trend over time exceeds an expected change over time and the sum of the pre-assigned numerical score values associated with each of the answers exceeds a threshold, then the processing computer issues an alert.

25. A system for monitoring a patient, with a previously diagnosed chronic condition comprising:
(a) a monitoring apparatus at a first location comprising:
a transducing device that generates an electronic signal representative of a physiological parameter of the patient;
a processor operatively coupled to the transducing device and programmed to process the electronic signals from the transducing device;
a communication device operatively coupled to the processor and to a communication network, the communication device including a transceiver having two portions, the first portion being operatively coupled to the processor and in communication with the second portion, the second portion being located remotely from the first portion and operatively coupled to the communication network;
an output device operatively coupled to the processor, the output device being configured to present questions to the patient that establish whether the patient is perceiving symptoms related to the previously diagnosed chronic condition, wherein the output device includes a synthetic speech communication device operable to audibly communicate information to the patient, and wherein the output device includes a visual display device;
an input device operatively coupled to the processor, the input device being configured to receive answers from the patient in response to the questions, each of the answers having a pre-assigned score value, wherein the score includes a numerical score; and
(b) a processing computer at a remote location, the processing computer communicatively coupled with the monitoring apparatus,
wherein the processing computer receives the processed electronic signal, thereby providing a source of physiological data, and also receives the answers, thereby providing a source of symptom data,
wherein the processing computer analyzes physiological data and symptom data over time; and
if at least one of a trend of the physiological data exceeds an expected change and a sum of the pre-assigned numerical score values associated with each of the answers exceeds a threshold, then the processing computer issues an alert.

26. The system of claim 1, wherein the issued alert notifies a caregiver that the patient requires attention.

27. The system of claim 1, wherein the issued alert includes the physiological data trend over time and symptom data.

28. A system for monitoring a patient with a previously diagnosed chronic condition and transferring information from a first location to a remote location, the system comprising:
(a) a portable monitoring apparatus at the first location comprising:
a transducing device that generates an electronic signal representative of a physiological parameter of the patient;
a processor operatively coupled to the transducing device and programmed to process the electronic signal;
a communication device operatively coupled to the processor and to a communication network;
an output device operatively coupled to the processor programmed to present questions to the patient that establish whether the patient is perceiving symptoms related to the previously diagnosed chronic condition;
an input device operatively coupled to the processor, the input device being configured to receive answers from the patient in response to the questions; and
(b) a processing computer at the remote location, the processing computer communicatively coupled with the monitoring apparatus,
wherein the processing computer:
receives the processed electronic signal, and also receives an indication of each of the answers, and
analyzes a trend of the physiological parameter based on the processed electronic signal and an overall symptom data score,
wherein the overall symptom data score is generated based on pre-assigned score values associated with each of the answers, and if the physiological data trend and the overall symptom data score exceeds an expected change over time, then the processing computer issues an alert.

* * * * *